US010611751B2

United States Patent
Hilliard et al.

(10) Patent No.: US 10,611,751 B2
(45) Date of Patent: Apr. 7, 2020

(54) DOPAMINE D1 RECEPTOR POSITIVE ALLOSTERIC MODULATORS

(71) Applicant: Eli Lilly and Company, Indianapolis, IN (US)

(72) Inventors: Darryl Wayne Hilliard, Fishers, IN (US); Junliang Hao, Carmel, IN (US); David Andrew Coates, New Palestine, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/386,684

(22) Filed: Apr. 17, 2019

(65) Prior Publication Data
US 2019/0322639 A1    Oct. 24, 2019

Related U.S. Application Data

(60) Provisional application No. 62/660,622, filed on Apr. 20, 2018.

(51) Int. Cl.
| | |
|---|---|
| *C07D 217/06* | (2006.01) |
| *C07D 401/06* | (2006.01) |
| *A61K 31/4725* | (2006.01) |
| *C07D 401/04* | (2006.01) |
| *A61P 25/18* | (2006.01) |
| *A61P 25/16* | (2006.01) |
| *A61P 25/28* | (2006.01) |

(52) U.S. Cl.
CPC ............ *C07D 401/04* (2013.01); *A61P 25/16* (2018.01); *A61P 25/18* (2018.01); *A61P 25/28* (2018.01); *C07B 2200/13* (2013.01)

(58) Field of Classification Search
CPC .............. A61K 31/4725; C07D 217/06; C07D 401/06; C07D 403/06
USPC ...................... 546/139, 146; 514/252.04, 307
See application file for complete search history.

(56) References Cited

U.S. PATENT DOCUMENTS

| | | | |
|---|---|---|---|
| 5,236,934 | A | 8/1993 | VanAtten |
| 8,962,654 | B2 | 2/2015 | Beadle et al. |
| 2006/0287359 | A1 | 12/2006 | Danso-Danquah et al. |
| 2014/0315963 | A1 | 10/2014 | Shiraki et al. |
| 2017/0304292 | A1 | 10/2017 | Valade et al. |
| 2017/0313677 | A1 | 11/2017 | Skolc et al. |
| 2018/0185383 | A1 | 7/2018 | Kawakami et al. |

FOREIGN PATENT DOCUMENTS

| | | |
|---|---|---|
| EP | 330360 A1 | 2/1989 |
| WO | 01/85695 A1 | 11/2001 |
| WO | 2016055479 * | 4/2016 |
| WO | 2016/204268 A1 | 12/2016 |
| WO | 2017/070068 A1 | 4/2017 |
| WO | 2017/178377 A1 | 10/2017 |
| WO | 2018/234232 A1 | 12/2018 |
| WO | 2019/173437 A1 | 9/2019 |
| WO | PCT/US2019/027842 A1 | 10/2019 |

OTHER PUBLICATIONS

Lin et al, Identification of a lead pharmacophore for the development of potent nuclear receptor modulators as anticancer and X syndrome disease therapeutic agents. Bioorganic & Medicinal Chemistry Letters 16, (2006), pp. 4178-4184.
Lewis, et al. Discovery of D1 Dopamine Receptor Positive Allosteric Modulators: Characterization of Pharmacology and Identification of Residues that Regulate Species Selectivity, J. Pharmacol. Exp. Ther. 2015, 354, 340-349.
Svensson, et al., An Allosteric Potentiator of the Dopamine D1 Receptor Increases Locomotor Activity in Human D1 Knock-In Mice without Causing Stereotypy or Tachyphylaxis. J. Pharmacol. Exp. Ther. 2017, 360, 117-128.
Bruns, et al., Preclinical Profile of a Dopamine D1 Potentiator Suggests Therapeutic Utility in Neurological and Psychiatric Disorders. Neuropharmacology 2018, 128, 351-365.
Wang, et al. Intracellular Binding Site for a Positive Allosteric Modulator of the Dopamine D1 Receptor. Mol. Pharmacol. 2018, 94, 1232-1245.
Luderman, et al., Identification of Positive Allosteric Modulators of the D1 Dopamine Receptor that Act at Diverse Sites. Mol. Pharmacol. 2018, 94, 1197-1209.
Hall et al. Novel Strategies to Activate the Dopamine D1 Receptor: Recent Advances in Orthosteric Agonism and Positive Allosteric Modulation, J. Med. Chem. 2019, 62, 128-140.

(Continued)

*Primary Examiner* — Niloofar Rahmani
(74) *Attorney, Agent, or Firm* — Danny Lee Wood

(57) ABSTRACT

The invention provides certain (phenyl)-(pyrazol)-3,4-dihydroisoquinolin-2(1H)-yl)ethan-1-one compounds of formula I as D1 positive allosteric modulators (PAMs), and pharmaceutical compositions thereof. The invention further provides methods of using a compound of formula I, or a pharmaceutically acceptable salt thereof, to treat certain symptoms of Parkinson's disease, schizophrenia, ADHD or Alzheimer's disease.

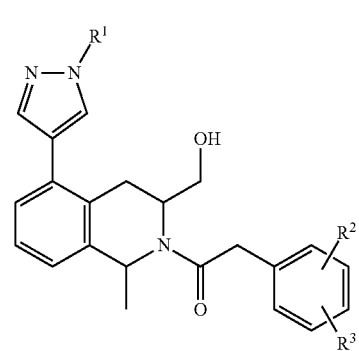

16 Claims, No Drawings

(56) References Cited

OTHER PUBLICATIONS

WO 2014/193784, U.S. Appl. No. 14/287,239, U.S. Pat. No. 8,962,654.
U.S. Appl. No. 62/781,251.
U.S. Appl. No. 62/904,048.
U.S. Appl. No. 62/916,330.
U.S. Appl. No. 62/915,330, filed Oct. 17, 2019 by Eli Lilly and Company, and commonly owned by Eli Lilly and Company.

* cited by examiner

DOPAMINE D1 RECEPTOR POSITIVE ALLOSTERIC MODULATORS

The invention provides certain (phenyl)-(pyrazol)-3,4-dihydroisoquinolin-2(1H)-yl)ethan-1-one compounds, pharmaceutical compositions thereof, and methods for their use in the treatment of Parkinson's disease, Alzheimer's disease, Schizophrenia, and Attention deficit hyperactivity disorder (ADHD).

Many currently used drugs work directly or indirectly through dopamine receptors. These include dopamine agonists and the dopamine precursor L-DOPA for Parkinson's disease, dopamine releasers for attention deficit disorder and narcolepsy, and dopamine reuptake inhibitors for depression. The D1 receptor has an important role in motor activity and reward, and a special role in maintaining higher cognitive functions for working memory, attention, and executive functions (Arnsten A F, *Cereb. Cortex* (2013) 123, 2269-2281). Attempts to develop D1 agonists for clinical use have so far not been successful, giving impetus to the search for alternative approaches to augmenting D1 receptor activity.

One such approach is to identify an allosteric potentiator, also known as a positive allosteric modulator or PAM, of the dopamine D1 receptor. (Svensson K, et al., *J. Pharmacol. Exp. Ther.* (2017) 360:117-128). Allosteric modulators are agents that either potentiate (Positive Allosteric Modulator, or PAM), or inhibit (Negative Allosteric Modulator, or NAM) the effect of the natural ligand by binding to a site that is distinct from the orthosteric binding site on the receptor (the allosteric binding site). By increasing the affinity of dopamine for the D1 receptor, a D1 potentiator may amplify the response to endogenous dopamine, increasing D1 tone when and where dopamine is released. This mode of activity is in contrast to a D1 agonist, which will activate all D1 receptors to which it has access for as long as it is present. In animal models of cognition and locomotor activity, D1 agonists show bell-shaped dose-response relationships, which are probably due to overstimulation at higher doses. Some D1 agonists also show rapid development of tolerance due to constant activation of the D1 receptor. In contrast, because a D1 potentiator would be dependent on endogenous tone and subject to normal feedback control, it may have a much lower propensity for overstimulation. Given the involvement of dopamine and D1 receptor signaling in these central nervous system functions, a D1 potentiator which can augment D1 receptor activity may provide an alternative and/or improved agent for the treatment of certain dopamine related diseases.

Parkinson's disease is a chronic, progressive, neurodegenerative disorder characterized by the loss of dopaminergic neurons in the brain. Parkinson's disease manifests in resting tremor along with other motor symptoms (e.g. bradykinesia and postural instability) and non-motor symptoms (e.g. cognitive impairment, sleep disorders, and depression). Current therapies for the treatment of Parkinson's disease include administration of non-selective dopamine precursors such as levodopa, and dopamine receptor agonists. Direct acting dopamine receptor agonist therapies may also be associated with impulse control disorders, psychosis, and worsening of cognition, due to their relatively greater affinity for D2 receptors. Schizophrenia is a debilitating disease with complex pathological mechanisms. A component of Schizophrenia is cognitive impairment, which may be associated with a deficiency in D1 receptor activation or D1 receptor down regulation. It has been hypothesized that D1 activation, selective over D2 modulation, may be effective in the treatment of cognitive impairment associated with schizophrenia. Alzheimer's disease is a chronic, progressive, neurodegenerative disorder characterized by loss of neurons and synapses in the cerebral cortex and certain subcortical regions. Disease progression includes cognitive impairment, which is hypothesized to be due at least in part to reduced D1 receptor activation; such that D1 activation may provide therapeutic benefit in the treatment of cognitive impairment associated with Alzheimer's disease. ADHD is a neurodevelopmental disorder characterized by difficulties with focused attention, excessive activity, or difficulty in controlling one's behavior as appropriate for the person's age. It is hypothesized that D1 activation may provide therapeutic benefit in the treatment of ADHD. Thus, there remains a significant unmet need for safe and effective treatment of cognitive or other neurological impairments associated with schizophrenia, Parkinson's disease, Alzheimer's disease and/or ADHD, such as alternative and/or improved dopamine D1 receptor positive allosteric modulators (D1 PAM's).

WO 2014/193781 recites certain 3,4-dihydroisoquinolin-2(1H)-yl compounds as D1 PAMs for the treatment of cognitive impairment associated with Parkinson's disease, Alzheimer's disease, schizophrenia, depression or ADHD.

The present invention provides certain novel compounds that are selective PAMs of the dopamine 1 receptor (D1) and demonstrate an advantageous combination of pharmacological properties, such as potentiation of human D1 receptor signaling in response to dopamine, high oral in vivo availabilty, and in vivo efficacy in locomotor activation of animals that are habituated to the environment. As such, compounds of the present invention are believed to be useful in the treatment of Parkinson's disease, Alzheimer's disease, schizophrenia, and/or ADHD. The compounds of the present invention may provide an alternative treatment for such disorders.

The present invention provides a compound of formula I:

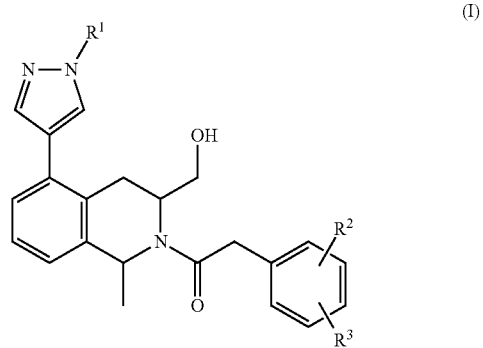

(I)

wherein:

$R^1$ is —H, —CH$_3$, —CH$_2$CH$_3$, —CH$_2$CH$_2$OH,

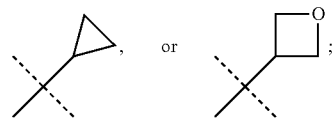

$R^2$ is —F or —Cl; and
$R^3$ is —H, —F or —Cl;
or a pharmaceutically acceptable salt thereof.

The compounds of formula I, or pharmaceutically acceptable salts thereof are particularly useful in the treatment methods of the invention, but certain configurations are preferred. The following paragraphs describe such preferred configurations. Although the present invention as embodied in formula I contemplates all individual enantiomers and diastereomers, as well as mixtures of diastereomers and mixtures of enantiomers of said compounds, including racemates, compounds with the absolute configuration as set forth below are preferred. It is understood that these preferences are applicable to the treatment methods and to the new compounds of the invention, and the pharmaceutically acceptable salts thereof.

A particular compound of formula I is a compound of formula Ia:

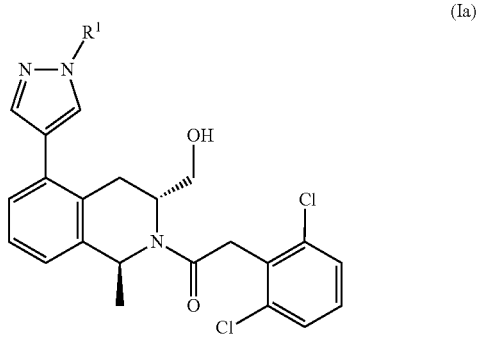

wherein:
R¹ is —H, —CH₃, —CH₂CH₃, —CH₂CH₂H,

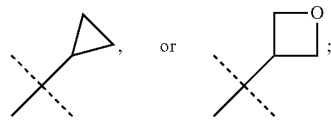

or a pharmaceutically acceptable salt thereof.

A particular compound of formula I is a compound of formula Ib:

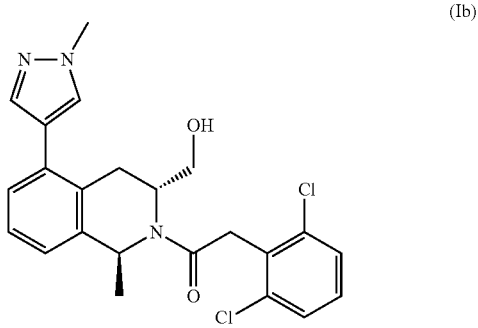 [SMILES: C[C@H]1c2cccc(-c3cnn(C)c3)c2C[C@H](CO)N1C(=O)Cc1c(Cl)cccc1Cl]

or a pharmaceutically acceptable salt thereof, which in the free base form can also be named as 2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one.

Further, the present invention provides a pharmaceutical composition comprising a compound of formula I, Ia, and/or Ib, or a pharmaceutically acceptable salt thereof, and a pharmaceutically acceptable carrier, diluent or excipient.

The following particular embodiments are compounds and/or salts of formula I, Ia, and/or Ib.

The present invention provides a compound which is 2-(2,6-dichlorophenyl)-1-((1S,3R)-5-(1-ethyl-1H-pyrazol-4-yl)-3-(hydroxymethyl)-1-methyl-3,4-dihydroisoquinolin-2(1H)-yl)ethan-1-one, or a pharmaceutically acceptable salt thereof.

The present invention provides a compound which is 1-((1S,3R)-5-(1-cyclopropyl-1H-pyrazol-4-yl)-3-(hydroxymethyl)-1-methyl-3,4-dihydroisoquinolin-2(1H)-yl)-2-(2,6-dichlorophenyl)ethan-1-one, or a pharmaceutically acceptable salt thereof.

The present invention provides a compound which is 2-(2,6-dichlorophenyl)-1-((1S,3R)-3-(hydroxymethyl)-1-methyl-5-(1-(oxetan-3-yl)-1H-pyrazol-4-yl)-3,4-dihydroisoquinolin-2(1H)-yl)ethan-1-one, or a pharmaceutically acceptable salt thereof.

The present invention provides a compound which is 1-((1S,3R)-5-(1-(2-(l1-oxidaneyl)ethyl)-1H-pyrazol-4-yl)-3-(hydroxymethyl)-1-methyl-3,4-dihydroisoquinolin-2(1H)-yl)-2-(2-chlorophenyl)ethan-1-one, or a pharmaceutically acceptable salt thereof.

The present invention provides a compound which is 2-(2-chloro-6-fluorophenyl)-1-((1S,3R)-3-(hydroxymethyl)-1-methyl-5-(1-(oxetan-3-yl)-1H-pyrazol-4-yl)-3,4-dihydroisoquinolin-2(1H)-yl)ethan-1-one, or a pharmaceutically acceptable salt thereof.

The present invention provides a compound which is 2-(2-chlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one, or a pharmaceutically acceptable salt thereof.

The present invention provides a compound which is 2-(2,6-dichlorophenyl)-1-((1S,3R)-3-(hydroxymethyl)-1-methyl-5-(1H-pyrazol-4-yl)-3,4-dihydroisoquinolin-2(1H)-yl)ethan-1-one, or a pharmaceutically acceptable salt thereof.

The present invention provides a compound which is 2-(2-chloro-6-fluorophenyl)-1-((1S,3R)-3-(hydroxymethyl)-1-methyl-5-(1H-pyrazol-4-yl)-3,4-dihydroisoquinolin-2(1H)-yl)ethan-1-one, or a pharmaceutically acceptable salt thereof.

The present invention provides a compound which is 2-(2,6-difluorophenyl)-1-((1S,3R)-3-(hydroxymethyl)-1-methyl-5-(1H-pyrazol-4-yl)-3,4-dihydroisoquinolin-2(1H)-yl)ethan-1-one, or a pharmaceutically acceptable salt thereof.

The present invention provides a compound which is 2-(2-chloro-5-fluorophenyl)-1-((1S,3R)-3-(hydroxymethyl)-1-methyl-5-(1H-pyrazol-4-yl)-3,4-dihydroisoquinolin-2(1H)-yl)ethan-1-one, or a pharmaceutically acceptable salt thereof.

The present invention provides a compound which is 2-(2-chloro-4-fluorophenyl)-1-((1S,3R)-3-(hydroxymethyl)-1-methyl-5-(1H-pyrazol-4-yl)-3,4-dihydroisoquinolin-2(1H)-yl)ethan-1-one, or a pharmaceutically acceptable salt thereof.

The present invention provides a compound which is 2-(2-fluorophenyl)-1-((1S,3R)-3-(hydroxymethyl)-1-methyl-5-(1H-pyrazol-4-yl)-3,4-dihydroisoquinolin-2(1H)-yl)ethan-1-one, or a pharmaceutically acceptable salt thereof.

The present invention provides a compound which is 2-(2,3-difluorophenyl)-1-((1S,3R)-3-(hydroxymethyl)-1- methyl-5-(1H-pyrazol-4-yl)-3,4-dihydroisoquinolin-2(1H)-yl)ethan-1-one, or a pharmaceutically acceptable salt thereof.

The present invention provides a compound which is 2-(2,5-difluorophenyl)-1-((1S,3R)-3-(hydroxymethyl)-1-methyl-5-(1H-pyrazol-4-yl)-3,4-dihydroisoquinolin-2(1H)-yl)ethan-1-one, or a pharmaceutically acceptable salt thereof.

Further, the present invention provides a compound and/or salt of one of the particular embodiments of the preceding list immediately above, and a pharmaceutically acceptable carrier, diluent or excipient.

Compounds of the present invention are selective PAMs of the dopamine 1 (D1) receptor with minimal activity at the dopamine 2 (D2) receptor. The compounds of present invention may further provide their therapeutic benefits while avoiding risks of drug-drug interactions. As such, compounds of the present invention are believed to be useful for the treatment of conditions in which reduced D1 activity plays a role, and D2 activation is undesirable, such as Parkinson's disease and schizophrenia, including relief of certain associated symptoms such as motor symptoms and cognitive impairment associated with Parkinson's disease and cognitive impairment and negative symptoms associated with schizophrenia, as for example mild cognitive impairment or dementia. Compounds of the present invention are also believed to be useful in improving motor symptoms in Parkinson's disease as a monotherapy or in combination with other therapies. Compounds of the present invention are also believed to be useful in treating certain symptoms of Alzheimer's disease such as cognitive impairment, as for example mild cognitive impairment. Further, compounds of the present invention are believed to be useful in treating certain symptoms of ADHD.

Further, the present invention provides a compound of formula I, or a pharmaceutically acceptable salt thereof, for use in therapy. Further, the present invention provides a compound of formula Ia, or a pharmaceutically acceptable salt thereof, for use in therapy. Further, the present invention provides a compound of formula Ib, or a pharmaceutically acceptable salt thereof, for use in therapy.

In another aspect the present invention provides a pharmaceutical composition comprising the compound of formula I, Ia or Ib, and one or more pharmaceutically acceptable carriers, diluents, or excipients. Furthermore, this aspect, of the invention provides a pharmaceutical composition for treating Parkinson's disease, as for example, cognitive impairment associated with Parkinson's disease, comprising the compound of formula I, Ia or b, and one or more pharmaceutically acceptable excipients, carriers, or diluents. In another embodiment of this aspect of the invention, there is provided a pharmaceutical composition for mitigating motor impairment associated with Parkinson's disease, comprising a compound of formula I, Ia or b, and one or more pharmaceutically acceptable excipients, carriers, or diluents.

In another embodiment of this aspect of the invention, there is provided a pharmaceutical composition for treating Alzheimer's disease, as for example mitigating cognitive impairment associated with Alzheimer's disease, comprising a compound of formula I, Ia or b, and one or more pharmaceutically acceptable excipients, carriers, or diluents.

Another embodiment of this aspect of the invention provides a pharmaceutical composition for treating schizophrenia, as for example mitigating cognitive impairment associated with schizophrenia, comprising the compound of formula I, Ia or b, and one or more pharmaceutically acceptable excipients, carriers, or diluents.

Another embodiment of present invention provides a pharmaceutical composition for treating ADHD, comprising the compound of formula I, Ia or b, and one or more pharmaceutically acceptable excipients, carriers, or diluents.

Further, the present invention provides a method of treating Parkinson's disease, as for example, cognitive impairment associated with Parkinson's disease, or for example, mitigating motor impairment associated with Parkinson's disease, comprising administering to a patient in need thereof an effective amount of a compound of formula I, Ia or Ib.

Further, the present invention provides a method of treating Alzheimer's disease, as for example, cognitive impairment associated with Alzheimer's disease, comprising administering to a patient in need thereof an effective amount of a compound of formula I, Ia or Ib.

Further, the present invention provides a method of treating schizophrenia, as for example, cognitive impairment associated with schizophrenia, comprising administering to a patient in need thereof an effective amount of a compound of formula I, Ia or Ib.

Further, the present invention provides a method of treating ADHD, comprising administering to a patient in need thereof an effective amount of a compound of formula I, Ia or Ib.

In one embodiment of this aspect, the present invention provides a compound of formula I, Ia or Ib, for use in the treatment of Parkinson's disease. In one particular embodiment the invention provides a compound of formula I, Ia or b, for use in the treatment of cognitive impairment associated with Parkinson's disease. In another particular embodiment the invention provides a compound of formula I, Ia or Ib, for use in mitigating motor impairment associated with Parkinson's disease.

Further, the present invention provides a compound of formula I, Ia or Ib, for use in the treatment of schizophrenia, as for example in the treatment of cognitive impairment associated with schizophrenia.

Further, the present invention provides a compound of formula I, Ia or Ib, for use in the treatment of ADHD.

Further, the present invention provides a compound of formula I, Ia or Ib, for use in the treatment of Alzheimer's disease, as for example in the treatment of cognitive impairment associated with Alzheimer's disease.

In yet another aspect, the present invention provides the use of a compound of formula I, Ia or Ib, in the manufacture of a medicament for the treatment of Parkinson's disease, as for example the treatment of cognitive impairment associated with Parkinson's disease, or the mitigation of motor impairment associated with Parkinson's disease.

Further, the present invention provides the use of a compound of formula I, Ia or Ib, in the manufacture of a medicament for the treatment of schizophrenia, as for example the treatment of cognitive impairment associated with schizophrenia.

Further, the present invention provides the use of a compound of formula I, Ia or Ib, in the manufacture of a medicament for the treatment of Alzheimer's disease, as for example the treatment of cognitive impairment associated with Alzheimer's disease.

Further, the present invention provides the use of a compound of formula I, Ia or Ib, in the manufacture of a medicament for the treatment of ADHD.

While it is possible to administer compounds employed in the methods of this invention directly without any formulation, the compounds are usually administered in the form of pharmaceutical compositions comprising the compound of formula I, Ia or Ib, as an active ingredient, and at least one pharmaceutically acceptable carrier, diluent and/or excipient. These compositions can be administered by a variety of routes including oral, sublingual, nasal, subcutaneous, intravenous, and intramuscular. Such pharmaceutical compositions and processes for preparing them are well known in the art. See, e.g., Remington: The Science and Practice of Pharmacy (University of the Sciences in Philadelphia, ed., 21st ed., Lippincott Williams & Wilkins Co., 2005).

The compositions are preferably formulated in a unit dosage form, each dosage containing from about 0.5 to about 800 mg of the active ingredient. The term "unit dosage form" refers to physically discrete units suitable as unitary dosages for human subjects and other mammals, each unit containing a predetermined quantity of active material calculated to produce the desired therapeutic effect, in association with at least one suitable pharmaceutically acceptable carrier, diluent and/or excipient. It will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms. It is contemplated that the compound of the invention, as for example in a pharmaceutical composition of the invention, will be used to treat Alzheimer's disease, Parkinson's disease and/or schizophrenia, as for example the treatment of mild cognitive impairment associated with these diseases, by chronic administration.

As used herein, the term "patient" refers to a mammal, as for example a human, in need of treatment for a disorder or disease. A human is a preferred patient.

As used herein, the terms "treatment", "treating", or "mitigating" are intended to refer to all processes wherein there may be a slowing, interrupting, arresting, controlling, or stopping of the progression of an existing disorder and/or a reduction in symptoms thereof, but does not necessarily indicate a total elimination of all symptoms.

As used herein, the term "effective amount" of a compound of formula I, Ia or Ib refers to an amount, that is a dosage, which is effective in potenitiating a dopamine mediated response in a patient. A preferred "effective amount" can be determined as an amount that can promote a wakeful or alert state in the patient as compared to the patient when untreated. In determining an effective amount or dose of a compound of formula I, Ia or Ib, a number of factors are considered, including, but not limited to the compound to be administered and its particular formulation; the patients size, age, and general health; the degree of involvement or the severity of the disorder; the response of the individual patient; the mode of administration; and other relevant circumstances.

"Pharmaceutically acceptable salts" or "a pharmaceutically acceptable salt" refers to the relatively non-toxic, inorganic and organic salt or salts of the compound of the present invention. It will be understood by the skilled artisan that compounds of the present invention are capable of forming salts. The compounds of the present invention contain basic heterocycles, and accordingly react with any of a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2008); S. M. Berge, et al., "Pharmaceutical Salts", *Journal of Pharmaceutical Sciences*, Vol 66, No. 1, January 1977.

Abbreviations used herein are defined as follows:
"ABT" means 1-aminobenzotriazole.
"AMPA" means α-amino-3-hydroxyl-5-methyl-4-isoxazole-propionic acid.
"Bn" means benzyl
"Brine" means saturated NaCl.
"BSA" means bovine serum albumin.
"cAMP" means cyclic adenosine monophosphate.
"CHO" means Chinese hamster ovary.
"DCM" means dichloromethane.
"DMEM" means Dulbecco's Minimum Eagle's Medium.
"DMSO" means dimethyl sulfoxide (perdeuterated [d6] if for NMR).
"$EC_x$" means the concentration of a test compound that produces the x % of the
maximum effect observed.
"EtOAc" means ethyl acetate.
"EtOH" means ethanol or ethyl alcohol.
"FBS" means Fetal Bovine Serum.
"HEPES" means 4-(2-hydroxyethyl)-1-piperazine ethanesulfonic acid.
"HTRF" means homogeneous time-resolved fluorescence.
"hr" means hour or hours.
"IBMX" means 3,7-dihydro-1-methyl-3-(2-methylpropyl)-1H-purine-2,6-dione.
"LCMS" means liquid chromatography mass spectrometry.
"LMA" means Locomotor Activity.
"MeOH" means methanol or methyl alcohol.
"min" means minutes.
"MOM" means methoxymethyl.
"MS" means mass spectroscopy or mass spectrum.
"PCR" means polymerase chain reaction.
"PG" means protecting group
"RAF" means relative activity factor.
"SEM" means standard error of the mean; "SEM, N" means standard error of the mean
followed by the number of data points.
"STIM" means Stimulation Buffer (as defined herein).
"THF" means tetrahydrofuran.
"TBDMS" means tert-butyldimethylsilyl.
"TBDPS" means tert-butyldiphenylsilyl.

General Chemistry

The compounds of the present invention can be prepared by general methods known and appreciated in the art or by processes described herein. Suitable reaction conditions for the steps of these schemes are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical.

Scheme 1

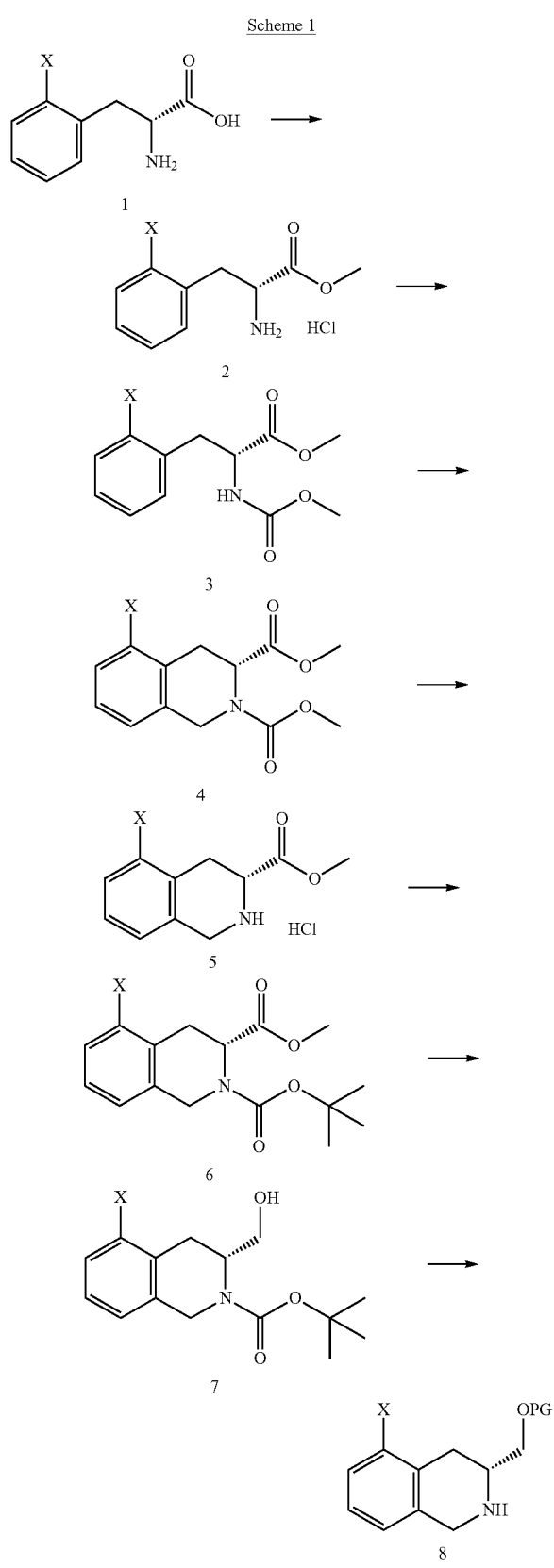

and appropriately 2-substituted phenylalanine 1 (e.g., X=Br, Cl, I), dissolved in a polar protic solvent may be esterified with a suitably strong acid to obtain the esterified salt 2. Subsequent acylation by washing the salt with aqueous base to obtain the free base, dissolving in an aprotic solvent, and adding the appropriate acid chloride may be accomplished to obtain 3. Cyclization of the 2-substituted N-acylated phenylalanine methyl ester 3 by treatment with paraformaldehyde in an appropriate strong acid and stirring to obtain the tetrahydroisoquinoline 4 is well known in the art. Demethylation and decarboxylation may be achieved by treatment with aqueous acid and stirring under reflux, to obtain 5 as the corresponding amine salt. One skilled in the art will recognize that N-protected tetrahydroisoquinoline 6 may be formed by dissolving amine salt 5 in the appropriate polar aprotic solvent, adding base and the suitable anhydride or alkyl chloroformate to obtain tertbutyl carbamate 6. Subsequent reduction to the methanol derivative 7 may be effected using an array of reducing agents, such as with a metal hydride, borohydride salt, or diborane in a polar aprotic solvent. O-protected tetrahydroisoquinoline 8 may be achieved by first treating the N-protected tetrahydroisoquinoline 7 with the appropriate strong acid and concentrating under vacuum. Thereafter, the amine salt may be dissolved in the appropriate aprotic solvent, treated with base and a suitable protecting group (PG) (e.g., PG=OSi, OBn, OMOM etc.) to provide 8. For example, protecting the primary alcohol with an acid stable silyl group such as TBDMS or TBDPS, is well known in the art.

Scheme 2

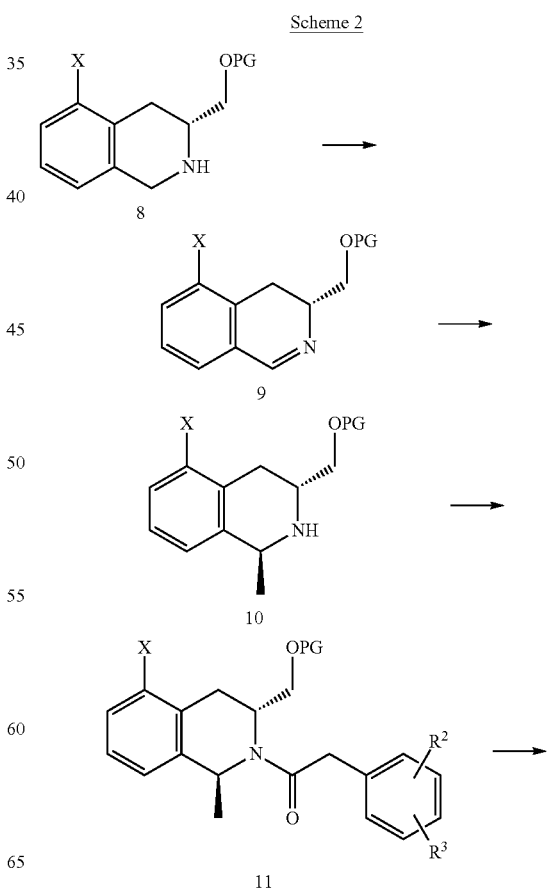

Scheme 1 depicts the preparation of compound 8. One skilled in the art will recognize the commercially available

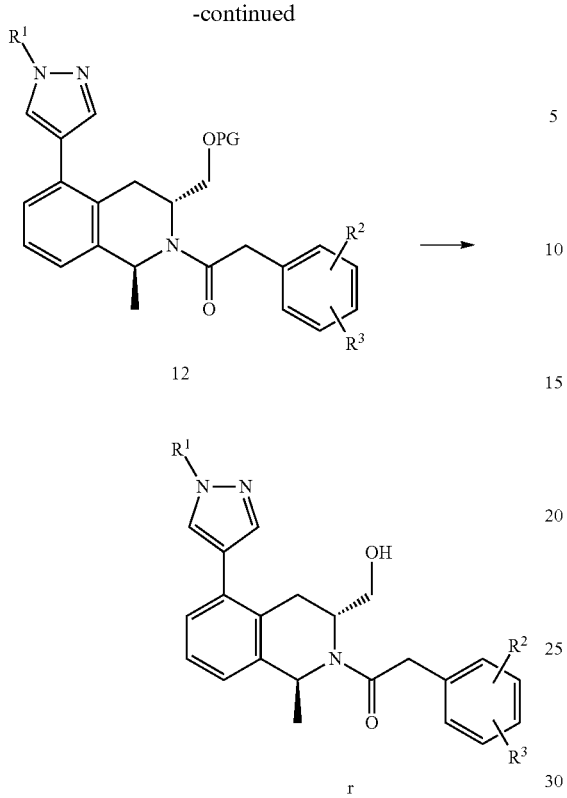

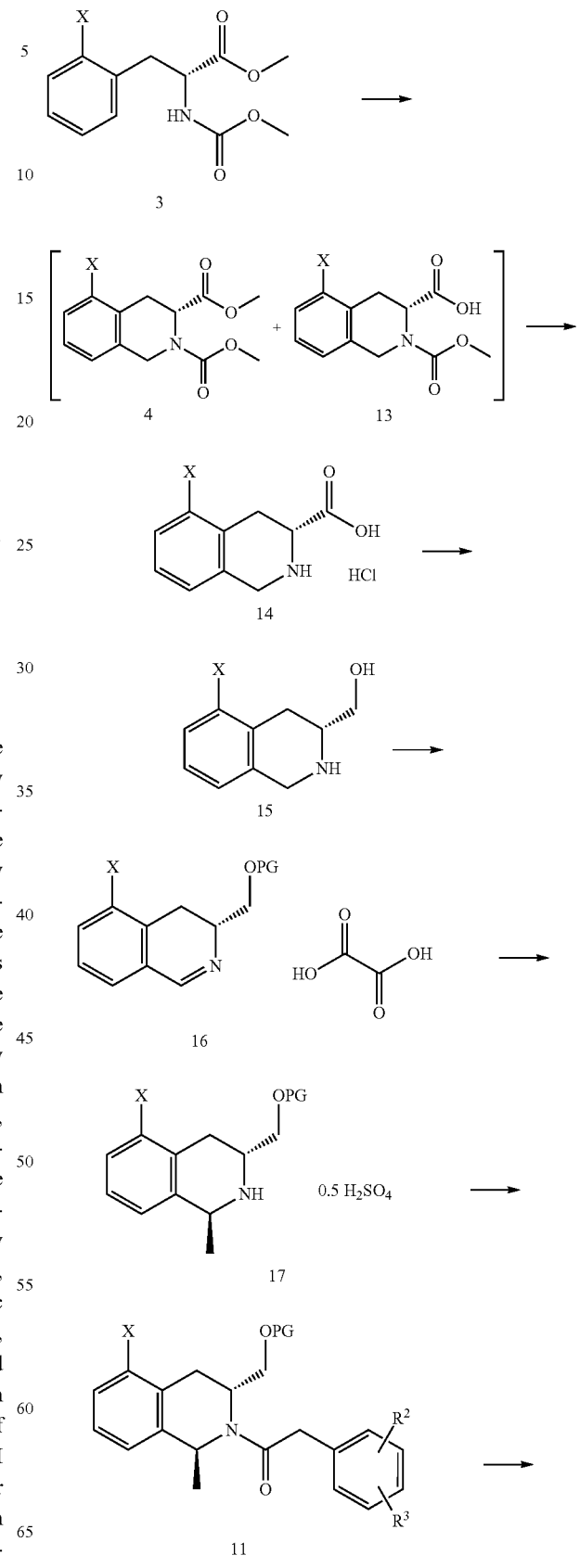

Scheme 3

Scheme 2 depicts the synthesis of the compounds of type I'. Imine formation from the tetrahydroisoquinoline 8 may be accomplished under various oxidative conditions recognizable to the skilled artisan, specifically halogenation of the secondary amine and subsequent elimination with a suitably strong base to provide dihydroisoquinoline 9. A stereoselective Grignard reaction may be used by treating the imine 9 with a suitable alkylmagnesium halide to obtain the trans tetrahydroisoquinoline 10. Relative configuration of the tetrahydroisoquinoline 10 may be determined with the appropriate NMR spectroscopic experiment, specifically 1D-NOESY. Subsequent N-acylation may be achieved with amide coupling techniques well known in the art, e.g., benzotriazol-1-yl-oxytripyrrolidinophosphonium hexafluorophosphate in the presence of a mild non-nucleophilic base to prepare compound 11. Aryl coupling using the appropriately substituted compound 11 (e.g., X=Br, Cl, I, etc.) may be effected under transition metal catalysis, such as using Pd, Pt, Ni, or Cu, with an appropriate aryl or heteroaryl boronic acid or ester, as is well known in the art. For example, Suzuki-coupling 11 with an appropriately substituted N-methylpyrrazoleboronate may be accomplished to obtain 12. The skilled artisan will recognize that the deprotection of the protected alcohol 12, wherein PG=OSi, OBn, OMOM etc., may be executed under a variety of conditions. For example, a silyl protecting group may be removed with tetrabutylammonium fluoride to obtain the chiral compounds of type I'.

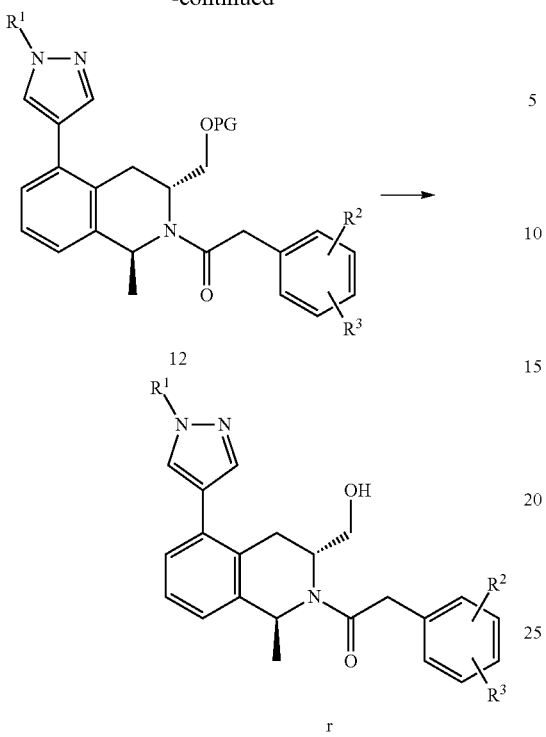

Scheme 3 depicts an alternative synthesis of the compounds of type I' wherein, at elevated temperatures, cyclization of the 2-substituted N-acylated phenylalanine methyl ester 3 by treatment with paraformaldehyde in an appropriate strong acid may produce a mixture of tetrahydroisoquinoline methyl ester 4 and carboxylic acid 13 as is evident to one adept in the art. The mixture of methyl ester 4 and carboxylic acid 13 may be subjected to the appropriate aqueous acid for complete ester hydrolysis to afford the carboxylic acid amine salt 14. Subsequent reduction to the methanol derivative 15 may be effected using an array of reducing agents, such as with a metal hydride, borohydride salt, or diborane in a polar aprotic solvent. O-protected dihydroisoquinoline 16 may be achieved by treatment with a suitable base and addition of the appropriate protecting group, previously described in Scheme 1 and as is common in the art, followed by halogenation of the secondary amine, subsequent elimination with a suitably strong base and stirring with oxalic acid to provide dihydroisoquinoline oxalate salt 16. A stereoselective methylation may be effected by first treating the imine oxalate salt 16 with aqueous base and extracting with a suitable organic solvent to afford the free base. A Grignard reaction may then be employed by treatment with the appropriate alkylmagnesium halide followed by stirring with concentrated sulfuric acid to obtain the trans tetrahydroisoquinoline hemi-sulfate 17. Relative configuration of the tetrahydroisoquinoline 17 may be determined with the appropriate NMR spectroscopic experiment, specifically 1D-NOESY. One skilled in the art will recognize that the trans tetrahydroisoquinoline hemisulfate 17 may be converted to the free base by addition of a suitable aqueous base and subsequent extraction with the appropriate organic solvent. N-acylation of said free base may be achieved with amide coupling techniques well known in the art, e.g., 1-propanephosphonic anhydride in the presence of a mild non-nucleophilic base to prepare compound 11. Aryl coupling using the appropriately substituted compound 11 (e.g., X=Br, Cl, I, etc.) may be effected under transition metal catalysis, such as using Pd, Pt, Ni, or Cu, with an appropriate aryl or heteroaryl boronic acid or ester, as is well known in the art. For example, Suzuki-coupling 11 with an appropriately substituted N-methylpyrrazoleboronate may be accomplished to obtain 12. The skilled artisan will recognize that the deprotection of the protected alcohol 12 similar to those described in Scheme 2, to provide compounds of type I'.

In the following illustrative preparations and examples, solvents are generally removed under reduced pressure (evaporated). In some procedures indicated yields are representative crude yields for products which are isolated by evaporation or filtration and used directly without further purification.

PREPARATION 1

Methyl 2-bromo-D-phenylalaninate hydrochloride

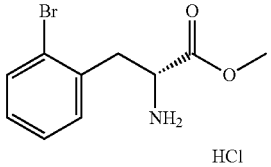

Dissolve 2-bromo-D-phenylalanine (22.4 g, 91.8 mmol) in MeOH (459 mL). Add acetyl chloride (65.3 mL, 917.7 mmol) at room temperature and stir for 36 hr. Concentrate under reduced pressure to give the title compound (27.2 g, >99% yield). MS: m/z 258/260 [M-Cl, $^{79}$Br/$^{81}$Br].

Alternatively, add acetyl chloride (562.79 g 7.17 mol) to MeOH (10.00 L) at 0° C. Heat the mixture to 17.5° C. and stir for 30 min. Add 2-bromo-D-phenylalanine (500.00 g, 2.05 moles) and heat to reflux for 4 hr. Cool the mixture to 20° C. and remove the solvent under reduced pressure to give the title compound (589 g, 96% yield) as an off-white solid. MS: m/z 258/260 [M-Cl, $^{79}$Br/$^{81}$Br].

PREPARATION 2

Methyl 2-bromo-N-(methoxycarbonyl)-D-phenylalaninate

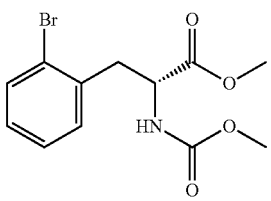 [SMILES: COC(=O)N[C@H](Cc1ccccc1Br)C(=O)OC]

Dissolve methyl 2-bromo-D-phenylalaninate hydrochloride (27.2 g, 92.3 mmol) in dichloromethane (923 mL) and water (185 mL). Add sodium bicarbonate (31.0 g 369.4 mmol) and methyl chloroformate (7.86 mL, 101.6 mmol) at room temperature and stir for 2.5 hr. Dilute with water and extract with dichloromethane. Dry the dichloromethane extracts over sodium sulfate, filter, and concentrate under reduced pressure. Purify the residue by silica gel chromatography eluting with EtOAc:hexanes (10-75% gradient) to give the title compound (29.1 g, >99% yield). MS: m/z 316/318 [M+H, $^{79}$Br/$^{81}$Br].

Alternatively, add water (2.94 L) and sodium hydrogen carbonate (648.25 g, 7.64 mol) to methyl 2-bromo-D-phenylalaninate hydrochloride (580 g, 1.91 mol) in dichloromethane (9.86 L) at 10° C. After 5 min add methyl chloroformate (198.5 g, 2.10 mol) and stir the mixture at 20° C. for 3 hr. Add water (2.5 L) and separate the layers.

Extract the aqueous fraction with dichloromethane, dry the combined organic extracts over sodium sulfate and concentrate under reduced pressure to give the title compound (556 g, 91% yield). MS (m/z): 315/317 [M+H, $^{79}$Br/$^{81}$Br].

PREPARATION 3

Dimethyl (3R)-5-bromo-3,4-dihydro-1H-isoquinoline-2,3-dicarboxylate

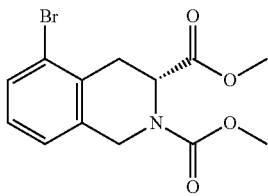 [SMILES: COC(=O)[C@H]1Cc2c(Br)cccc2CN1C(=O)OC]

Stir a mixture of methyl 2-bromo-N-(methoxycarbonyl)-D-phenylalaninate (29.1 g 92.1 mmol) and paraformaldehyde (9.13 g, 101.3 mmol) in glacial acetic acid (115 mL, 2.0 mol) and concentrated sulfuric acid (38.4 mL, 719.9 mmol) at room temperature for 7 hr.

Partition between water and EtOAc. Separate the layers and extract the aqueous layer with EtOAc. Combine the EtOAc extracts and dry over sodium sulfate, filter, and concentrate under reduced pressure. Purify the residue by silica gel chromatography eluting with EtOAc:hexanes (5-40% gradient) to give the title compound (27.6 g, 91% yield). MS: m/z 328/330 [M+H, $^{79}$Br/$^{81}$Br].

PREPARATION 3a

Dimethyl (3R)-5-bromo-3,4-dihydro-1H-isoquinoline-2,3-dicarboxylate (3a) and (3R)-5-bromo-2-methoxycarbonyl-3,4-dihydro-1H-isoquinoline-3-carboxylic acid (3b)

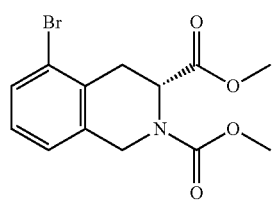

3a

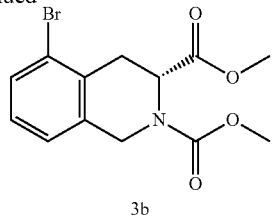

3b

Add methyl 2-bromo-N-(methoxycarbonyl)-D-phenylalaninate (572 g, 1.81 mol) and paraformaldehyde (205.9 g, 2.17 mol) to acetic acid (4.3 L) at 10° C. After 10 min, slowly add concentrated sulfuric acid (2.63 kg, 26.83 mol) and stir at 35° C. for 12 hr. Cool the reaction mixture to 15° C. and add water (7.5 L) and EtOAc (6 L). Separate the layers and re-extract the aqueous fraction with EtOAc (2.5 L). Dry the combined organic extracts over sodium sulfate, filter and concentrate under reduced pressure to give a mixture of the title compounds with acetic acid (640 g, >97% yield). MS (m/z): 3a: 328/330 [M+H, $^{79}$Br/$^{81}$Br], 3b: 314/316 [M+H, $^{79}$Br/$^{81}$Br].

PREPARATION 4

Methyl (3R)-5-bromo-1,2,3,4-tetrahydroisoquinoline-3-carboxylate hydrochloride

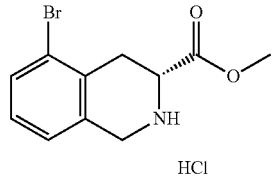

Dissolve dimethyl (3R)-5-bromo-3,4-dihydro-1H-isoquinoline-2,3-dicarboxylate (27.6 g 84.0 mmol) in 5 N HCl (330.6 mL, 1.7 mol) and heat to reflux for three days. Concentrate under reduced pressure to give a white solid. Wash the solid with diethyl ether and dry under vacuum at 40° C. overnight to give (3R)-5-bromo-1,2,3,4-tetrahydroisoquinoline-3-carboxylic acid hydrochloride (1:1) (20.8 g, 71.1 mmol). Add acetyl chloride (50.6 mL, 711.0 mmol) to a 0° C. mixture of (3R)-5-bromo-1,2,3,4-tetrahydroisoquinoline-3-carboxylic acid hydrochloride (1:1) (20.8 g, 71.1 mmol) in MeOH (474 mL). Warm to room temperature and stir for 36 hr. Concentrate under reduced pressure and dry to give the title compound (21.9 g, 85% yield). MS: m/z 270/272 [M-Cl, $^{79}$Br/$^{81}$Br].

PREPARATION 5

(3R)-5-Bromo-1,2,3,4-tetrahydroisoquinoline-3-carboxylic acid hydrochloride

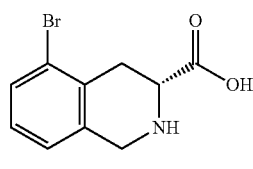

Add water (1.3 L) and 36.5% hydrochloric acid (9.1 kg, 90.8 moles) to a mixture of dimethyl (3R)-5-bromo-3,4-dihydro-1H-isoquinoline-2,3-dicarboxylate and (3R)-5-bromo-2-methoxycarbonyl-3,4-dihydro-1H-isoquinoline-3-carboxylic acid (520 g, 1.27 moles) and stir the mixture at 95° C. for 12 hr. Cool the mixture to 10° C. and stir for an additional 15 min. Filter the mixture and dry the solid under vacuum at 40° C. to give the title compound (332 g, 89% yield). MS (m/z): 256/258 [M-Cl, $^{79}$Br/$^{81}$Br].

PREPARATION 6

2-tert-Butyl-3-methyl-(3R)-5-bromo-3,4-dihydro-1H-isoquinoline-2,3-dicarboxylate

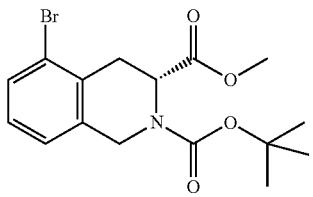 [SMILES: COC(=O)[C@H]1Cc2c(Br)cccc2CN1C(=O)OC(C)(C)C]

Dissolve methyl (3R)-5-bromo-1,2,3,4-tetrahydroisoquinoline-3-carboxylate hydrochloride (21.0 g 68.5 mmol) in 1,4-dioxane (685 mL). Add saturated sodium bicarbonate solution (685 mL, 17.5 mol) and di-tert-butyldicarbonate (29.9 g 137.0 mmol) at room temperature and stir the biphasic mixture for 90 min. Extract with EtOAc. Dry the EtOAc over sodium sulfate, filter, and concentrate under reduced pressure. Purify the residue by silica gel chromatography eluting with EtOAc:hexanes (5-50% gradient) to give the title compound (19.5 g, 77% yield). MS (m/z): 270/272 [M-$^t$Boc+H, $^{79}$Br/$^{81}$Br].

PREPARATION 7

[(3R)-5-Bromo-1,2,3,4-tetrahydroisoquinolin-3-yl]methanol

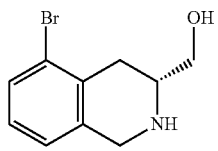 [SMILES: OC[C@H]1Cc2c(Br)cccc2CN1]

Add lithium aluminium hydride (2 L, 2.00 mol, 1M in THF) to (3R)-5-bromo-1,2,3,4-tetrahydroisoquinoline-3-carboxylic acid hydrochloride (325.4 g, 1.11 mol) in THF (4.88 L) at −35° C. Warm to 25° C. over 60 min with stirring. After 3 hr, cool the mixture to −5° C., add water (76 mL), add 15% w/w aqueous sodium hydroxide (76 mL), followed by additional water (228 mL). Heat the mixture to 25° C., add anhydrous magnesium sulfate (750 g) with stirring. Filter the mixture and concentrate under reduced pressure to give a solid. Add dichloromethane (690 mL) to the solid and slurry for 30 min before filtration to give a solid. Dry the solid under vacuum at 35° C. to give the title compound (148.9 g, 59% yield). MS (m/z): 242/244 [M+H, $^{79}$Br/$^{81}$Br].

PREPARATION 8 tert-Butyl (3R)-5-bromo-3-(hydroxymethyl)-3,4-dihydro-1H-isoquinoline-2-carboxylate

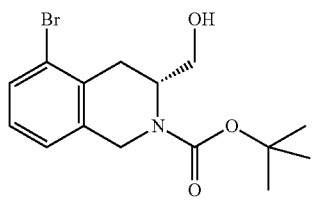 [SMILES: CC(C)(C)OC(=O)N1Cc2cccc(Br)c2C[C@@H]1CO]

Add methanol (10.1 mL, 248.5 mmol) and lithium borohydride (99.4 mL, 198.8 mmol, 2M in THF) to a solution of 2-tert-butyl-3-methyl-(3R)-5-bromo-3,4-dihydro-1H-isoquinoline-2,3-dicarboxylate (18.4 g, 49.7 mmol) in THF (497 mL) at room temperature on a water bath. Stir 40 min and quench the reaction with water. Extract with ethyl acetate.

Dry the ethyl acetate extracts over sodium sulfate, filter, and concentrate under reduced pressure. Purify the residue by silica gel chromatography eluting with ethyl acetate:hexanes (5-80% gradient). Dry under high vacuum overnight to give the title compound as a white solid (19.1 g, >99% yield). MS (m/z): 286/288 [M-$^t$Bu+H, $^{79}$Br/$^{81}$Br].

PREPARATION 9

[(3R)-5-Bromo-1,2,3,4-tetrahydroisoquinolin-3-yl]methoxy-tert-butyl-dimethyl-silane

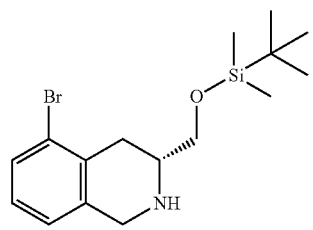 [SMILES: CC(C)(C)[Si](C)(C)OC[C@H]1Cc2c(Br)cccc2CN1]

Add trifluoroacetic acid (75.5 mL, 998.3 mmol) to solution of tert-butyl (3R)-5-bromo-3-(hydroxymethyl)-3,4-dihydro-1H-isoquinoline-2-carboxylate (15.5 g, 45.3 mmol) in dichloromethane (226 mL) at room temperature. Stir 30 min and concentrate under reduced pressure. Dry under vacuum to give [(3R)-5-bromo-1,2,3,4-tetrahydroisoquinolin-3-yl]methanol; 2,2,2-trifluoroacetic acid as a wet solid. Dissolve [(3R)-5-bromo-1,2,3,4-tetrahydroisoquinolin-3-yl]methanol; 2,2,2-trifluoroacetic acid in dichloromethane (753 mL). Add 1H-imidazole (51.3 g, 753 mmol), N,N-dimethyl-4-pyridinamine (460 mg, 3.77 mmol), and t-butyldimethylchlorosilane (13.6 g, 90.4 mmol). Stir at room temperature overnight. Add saturated ammonium chloride solution and extract with dichloromethane. Dry the dichloromethane extracts over sodium sulfate, filter, and concentrate under reduced pressure. Combine with the crude product from a substantially same reaction run with of tert-butyl (3R)-5-bromo-3-(hydroxymethyl)-3,4-dihydro-1H-isoquinoline-2-carboxylate (6.6 g, 19.4 mmol). Purify the residue by silica gel chromatography eluting with ethyl acetate:hexanes (5-40% gradient) to give the title compound (14.3 g, 89% yield). MS (m/z): 356/358 [M+H, $^{79}$Br/$^{81}$Br].

Alternative synthesis of [(3R)-5-bromo-1,2,3,4-tetrahydroisoquinolin-3-yl]methoxy-tert-butyl-dimethyl-silane Add tert-butyldimethylchlorosilane (193.7 g, 1.3 mol) to a mixture of [(3R)-5-bromo-1,2,3,4-tetrahydroisoquinolin-3-yl]methanol (148.9 g, 0.6 mol), 1H-imidazole (202.9 g, 2.92 mol), 4-dimethylaminopyridine (720 mg, 5.8 mmol) and N,N-dimethylformamide (1.04 L) in dichlormethane (2.61 L) at 20° C. and stir in an appropriate vessel. After 3 hours, cool the mixture to 10° C. and add saturated aqueous ammonium chloride solution (1.3 L).

Extract the aqueous with dichloromethane and wash the combined organic extracts with brine (2×2 L), dry over anhydrous sodium sulfate and concentrate under reduced pressure to give a residue. Dissolve the residue in methyl tert-butyl ether (1.5 L) and wash with brine (2×1 L). Dilute the organic phase with toluene (5 L) and concentrate under reduced pressure to give a residue. Add toluene (2.6 L) to the residue and concentrate under reduced pressure to give the title compound (210 g, 81% yield). MS (m/z). 356/358 [M+H, $^{79}$Br/$^{81}$Br].

PREPARATION 10

[(3R)-5-Bromo-3,4-dihydroisoquinolin-3-yl]methoxy-tert-butyl-dimethyl-silane

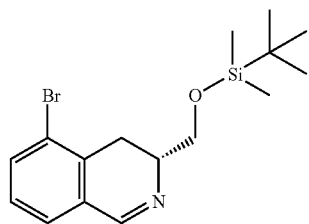 [SMILES: CC(C)(C)[Si](C)(C)OC[C@H]1Cc2c(Br)cccc2C=N1]

Dissolve [(3R)-5-bromo-1,2,3,4-tetrahydroisoquinolin-3-yl]methoxy-tert-butyl-dimethyl-silane (4.2 g, 11.8 mmol) in diethyl ether (118 mL). Add N-chlorosuccinimide (2.36 g, 17.7 mmol). Stir 30 min at room temperature and concentrate under reduced pressure. Dissolve the residue in potassium hydroxide (42.0 mL, 30.3 mmol, 5% in MeOH) and stir for 30 min at room temperature. Pour into water and extract with dichloromethane. Dry the dichloromethane extracts over sodium sulfate, filter, and concentrate under reduced pressure. Purify the residue by silica gel chromatography eluting with ethyl acetate:hexanes (5-100% gradient) to give the title compound (3.40 g, 82% yield). MS (m/z): 354/356 [M+H, $^{79}$Br/$^{81}$Br].

Alternative synthesis of [(3R)-5-bromo-3,4-dihydroisoquinolin-3-yl]methoxy-tert-butyl-dimethyl-silane Add N-chlorosuccinimide (106.7 g, 790 mmol) to a solution of [(3R)-5-bromo-3,4-dihydroisoquinolin-3-yl]methoxy-tert-butyl-dimethyl-silane. (220 g, 520 mmol) in tetrahydrofuran (3.85 L) at 20° C. in an appropriate vessel and stir. After 30 minutes concentrate the mixture under reduced pressure and dissolve the residues in 5% w/w potassium hydroxide in methanol (2.2 L, 1.7 moles) and stir at 20° C. After 30 minutes, add the mixture to water (3 L) and extract three times with dichloromethane (3×1 L). Dry the combined organic extracts over anhydrous magnesium sulfate and concentrate under reduced pressure to give the title compound (210 g, >99% yield). MS (m/z): 354/356 [M+H, $^{79}$Br/$^{81}$Br].

PREPARATION 11

[(1S,3R)-5-Bromo-1-methyl-1,2,3,4-tetrahydroisoquinolin-3-yl]methoxy-tert-butyl-dimethyl-silane

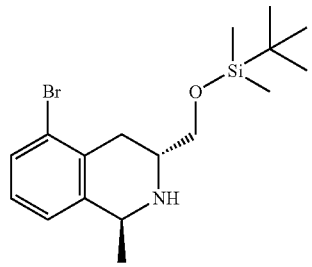 [SMILES: C[C@@H]1N[C@@H](CO[Si](C)(C)C(C)(C)C)Cc2c(Br)cccc21]

Dissolve [(3R)-5-bromo-3,4-dihydroisoquinolin-3-yl]methoxy-tert-butyl-dimethyl-silane (3.4 g, 9.6 mmol) in diethyl ether (160 mL). Cool to −78° C. on a dry ice-acetone bath. Add a 3M solution of methylmagnesium chloride in THF (26.9 mL, 80.6 mmol) dropwise. Warm the reaction mixture slowly to room temperature and stir overnight.

Quench with saturated ammonium chloride solution slowly. Extract with dichloromethane and dry over sodium sulfate, filter, and concentrate under reduced pressure. Combine with the crude product from a substantially same reaction run with 1.7 mmol of [(3R)-5-bromo-3,4-dihydroisoquinolin-3-yl]methoxy-tert-butyl-dimethyl-silane. Purify the combined residues by silica gel chromatography eluting with ethyl acetate:hexanes (5-65% gradient) to give the title compound (3.78 g, >99% yield). MS (m/z): 370/372 [M+H, $^{79}$Br/$^{81}$Br].

The relative configuration of compound [(1S,3R)-5-bromo-1-methyl-1,2,3,4-tetrahydroisoquinolin-3-yl]methoxy-tert-butyl-dimethyl-silane is determined by NMR spectroscopy using one-dimensional NOE experiments (1D-NOESY). Selective excitation of the methyl group at 1.30 ppm gives rise to a NOE for Ha at 3.11 ppm. This NOE enhancement is only consistent with a configuration in which the methyl and Ha are on the same side of the ring (trans isomer) because in the cis isomer the methyl protons are too far away from Ha to show an NOE. Since the absolute chemistry for position 3 is known to be R, then the absolute chemistry at position 1 is deduced to be S.

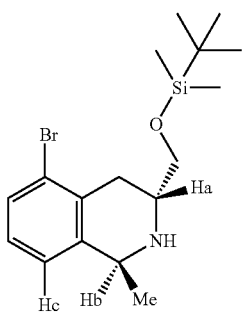

Alternative synthesis of [(1S,3R)-5-bromo-1-methyl-1,2,3,4-tetrahydroisoquinolin-3-yl]methoxy-tert-butyl-dimethyl-silane

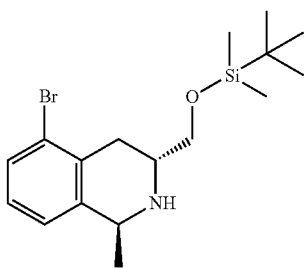 [SMILES: C[C@@H]1N[C@@H](CO[Si](C)(C)C(C)(C)C)Cc2c(Br)cccc21]

Add a 3M solution of methylmagnesium chloride in THF (0.66 L, 1.99 mol) to a solution of [(3R)-5-bromo-3,4-dihydroisoquinolin-3-yl]methoxy-tert-butyl-dimethyl-silane (93.5 g, 0.2 mol) in diethyl ether (2.8 L) at −65° C. in an appropriate vessel. Then heat the reaction mixture to 20° C. over 2 hours and stir. After 16 hours, cool the mixture to 0° C. and quench the reaction with saturated aqueous ammonium chloride solution (2.5 L) and extract with ethyl acetate (2.5 L) and filter the mixture. Wash the combined organic extracts with brine (1 L), dry over anhydrous magnesium sulfate and concentrate under reduced pressure to give the crude title compound as an oil. Combine the oil with crude products from substantially same reactions of [(3R)-5-bromo-3,4-dihydroisoquinolin-3-yl]methoxy-tert-butyl-dimethyl-silane and purify the pooled crude products by silica gel chromatography eluting with ethyl acetate in hexanes (gradient 5-65% ethyl acetate) to give the title compound (151 g, 97% yield, combined from 2 experimental runs). MS (m/z): 370/372 [M+H, $^{79}$Br/$^{81}$Br].

PREPARATION 12

1-[(1S,3R)-5-bromo-3-[[tert-butyl(dimethyl)silyl]oxymethyl]-1-methyl-3,4-dihydro-1H-isoquinolin-2-yl]-2-(2,6-dichlorophenyl)ethanone

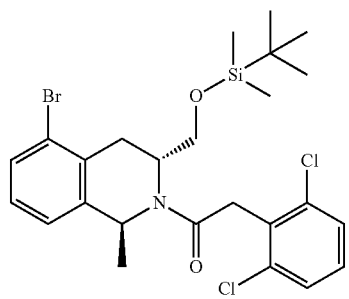 [SMILES: C[C@H]1c2cccc(Br)c2C[C@H](CO[Si](C)(C)C(C)(C)C)N1C(=O)Cc1c(Cl)cccc1Cl]

Add benzotriazol-1-yl-oxytripyrrolidinophosphonium hexafluorophosphate (7.9 g, 15.3 mmol) to a mixture of [(1S,3R)-5-bromo-1-methyl-1,2,3,4-tetrahydroisoquinolin-3-yl]methoxy-tert-butyl-dimethyl-silane (3.78 g, 10.2 mmol) and 2,6-dichlorophenylacetic acid (2.3 g, 11.2 mmol) in dimethylformamide (51.0 mL). Add triethylamine (2.1 mL, 15.3 mmol) and stir at room temperature 3 hours. Dilute with water and extract with dichloromethane. Dry the dichloromethane extracts over sodium sulfate, filter and concentrate under reduced pressure. Purify the residue by silica gel chromatography eluting with ethyl acetate:hexanes (5-50% gradient) to give the title compound (4.7 g, 55% yield). MS: m/z 556/558 [M+H, $^{35}$Cl/$^{37}$Cl)].

The following compounds are prepared essentially by the method of Preparation 12.

| Preparation No. | Name | Structure | Physical data |
|---|---|---|---|
| 13 | 1-((1S,3R)-5-bromo-3-(((tert-butyldimethylsilyl)oxy)methyl)-1-methyl-3,4-dihydroisoquinolin-2(1H)-yl)-2-(2-chloro-6-fluorophenyl)ethan-1-one | 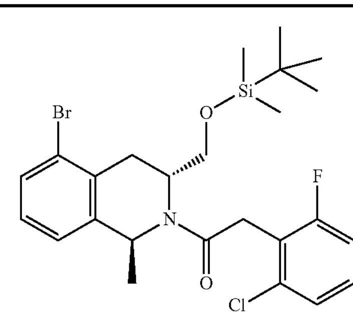 | MS (m/z): 540 (M + H) |

-continued

| Preparation No. | Name | Structure | Physical data |
|---|---|---|---|
| 14 | 1-((1S,3R)-5-bromo-3-(((tert-butyldimethylsilyl)oxy)methyl)-1-methyl-3,4-dihydroisoquinolin-2(1H)-yl)-2-(2-chloro-6-difluorophenyl)ethan-1-one | 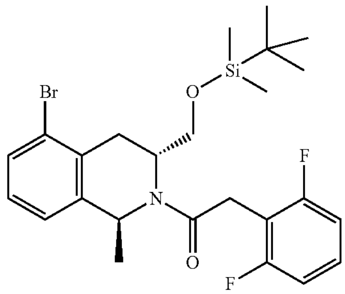 [SMILES: C[C@H]1c2cccc(Br)c2C[C@H](CO[Si](C)(C)C(C)(C)C)N1C(=O)Cc1c(F)cccc1F] | MS (m/z): 524 (M + H) |
| 15 | 1-((1S,3R)-5-bromo-3-(((tert-butyldimethylsilyl)oxy)methyl)-1-methyl-3,4-dihydroisoquinolin-2(1H)-yl)-2-(2-chloro-5-fluorophenyl)ethan-1-one | 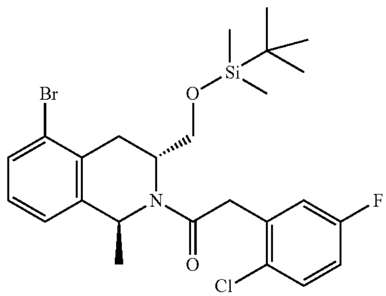 [SMILES: C[C@H]1c2cccc(Br)c2C[C@H](CO[Si](C)(C)C(C)(C)C)N1C(=O)Cc1cc(F)ccc1Cl] | MS (m/z): 540 (M + H) |
| 16 | 1-((1S,3R)-5-bromo-3-(((tert-butyldimethylsilyl)oxy)methyl)-1-methyl-3,4-dihydroisoquinolin-2(1H)-yl)-2-(2-chloro-4-fluorophenyl)ethan-1-one | 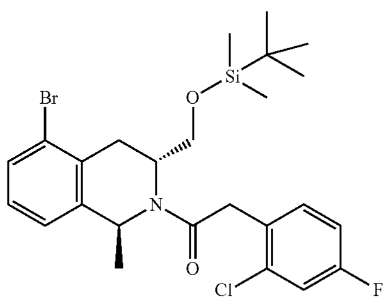 [SMILES: C[C@H]1c2cccc(Br)c2C[C@H](CO[Si](C)(C)C(C)(C)C)N1C(=O)Cc1ccc(F)cc1Cl] | MS (m/z): 540 (M + H) |
| 17 | 1-((1S,3R)-5-bromo-3-(((tert-butyldimethylsilyl)oxy)methyl)-1-methyl-3,4-dihydroisoquinolin-2(1H)-yl)-2-(2-fluorophenyl)ethan-1-one | 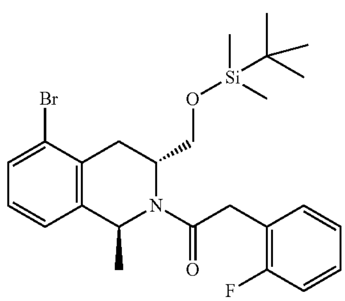 [SMILES: C[C@H]1c2cccc(Br)c2C[C@H](CO[Si](C)(C)C(C)(C)C)N1C(=O)Cc1ccccc1F] | MS (m/z): 506 (M + H) |
| 18 | 1-((1S,3R)-5-bromo-3-(((tert-butyldimethylsilyl)oxy)methyl)-1-methyl-3,4-dihydroisoquinolin-2(1H)-yl)-2-(2,3-difluorophenyl)ethan-1-one | 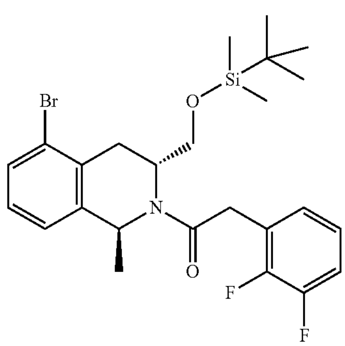 [SMILES: C[C@H]1c2cccc(Br)c2C[C@H](CO[Si](C)(C)C(C)(C)C)N1C(=O)Cc1cccc(F)c1F] | MS (m/z): 524 (M + H) |

| Preparation No. | Name | Structure | Physical data |
|---|---|---|---|
| 19 | 1-((1S,3R)-5-bromo-3-(((tert-butyldimethylsilyl)oxy)methyl)-1-methyl-3,4-dihydroisoquinolin-2(1H)-yl)-2-(2,5-difluorophenyl)ethan-1-one | 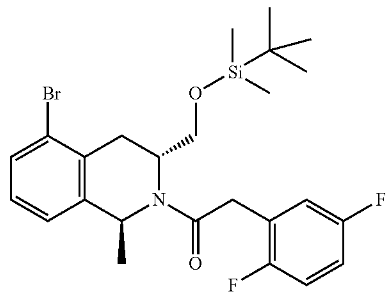 | MS (m/z): 524 (M + H) |
| 20 | 1-((1S,3R)-5-bromo-3-(((tert-butyldimethylsilyl)oxy)methyl)-1-methyl-3,4-dihydroisoquinolin-2(1H)-yl)-2-(2-chlorophenyl)ethan-1-one | 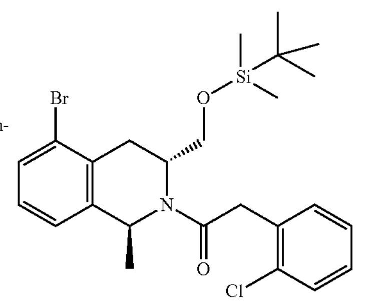 | MS (m/z): 522 (M + H) |

PREPARATION 21

1-((1S,3R)-3-(((tert-butyldimethylsilyl)oxy)methyl)-1-methyl-5-(1-methyl-1H-pyrazol-4-yl)-3,4-dihydroisoquinolin-2(1H)-yl)-2-(2,6-dichlorophenyl)ethan-1-one

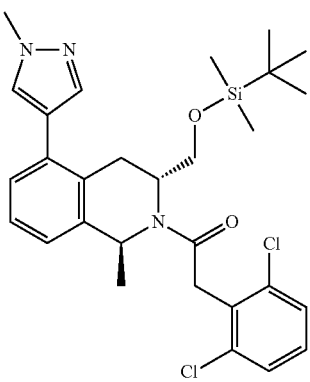 [SMILES: C[C@H]1c2cccc(-c3cnn(C)c3)c2C[C@H](CO[Si](C)(C)C(C)(C)C)N1C(=O)Cc1c(Cl)cccc1Cl]

Dissolve 1-((1S,3R)-5-bromo-3-(((tert-butyldimethylsilyl)oxy)methyl)-1-methyl-3,4-dihydroisoquinolin-2(1H)-yl)-2-(2,6-dichlorophenyl)ethan-1-one (200 mg; 0.4 mmoles) and 1-methyl-4-(4,4,5,5-tetramethyl-1,3,2-dioxa-2-yl)pyrazole (149 mg; 0.7 mmoles) in 1,4-dioxane (3.6 mL). Add a 0.2M aqueous solution of sodium carbonate (1.8 mL, 0/4 mmol) and bubble nitrogen for 10 min. Add bis(triphenylphosphine)palladium(II) chloride (50 mg, 72 μmoles). Heat to 90° C. for 2 h. Cool to ambient temperature, dilute with water, extract with EtOAc, dry over sodium sulfate, filter, concentrate and purify by silica gel chromatography eluting with a gradient from 5% to 50% EtOAc in hexanes to provide the title compound (195 mg, 97% yield). MS: m/z 558/560 [M+H, $^{35}Cl/^{37}Cl$].

The following compounds are prepared essentially by the method of Preparation 21 using 1-((1S,3R)-5-bromo-3-(((tert-butyldimethylsilyl)oxy)methyl)-1-methyl-3,4-dihydroisoquinolin-2(1H)-yl)-2-(2,6-dichlorophenyl)ethan-1-one and the appropriately substituted pyrazolo-boronic acid or boronic ester derivative.

| Preparation No. | Name | Structure | Physical data |
|---|---|---|---|
| 22 | 1-((1S,3R)-3-(((tert-butyldimethylsilyl)oxy)methyl)-5-(1-ethyl-1H-pyrazol-4-yl)-1-methyl-3,4-dihydroisoquinolin-2(1H)-yl)-2-(2,6-dichlorophenyl)ethan-1-one | 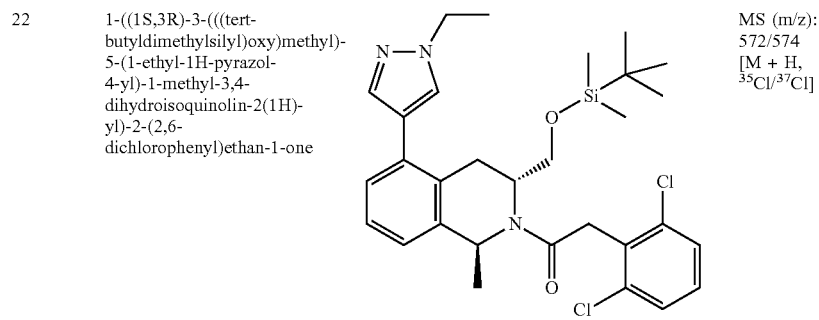 | MS (m/z): 572/574 [M + H, $^{35}$Cl/$^{37}$Cl] |
| 23 | 1-((1S,3R)-3-(((tert-butyldimethylsilyl)oxy)methyl)-5-(1-cyclopropyl-1H-pyrazol-4-yl)-1-methyl-3,4-dihydroisoquinolin-2(1H)-yl)-2-(2,6-dichlorophenyl)ethan-1-one | 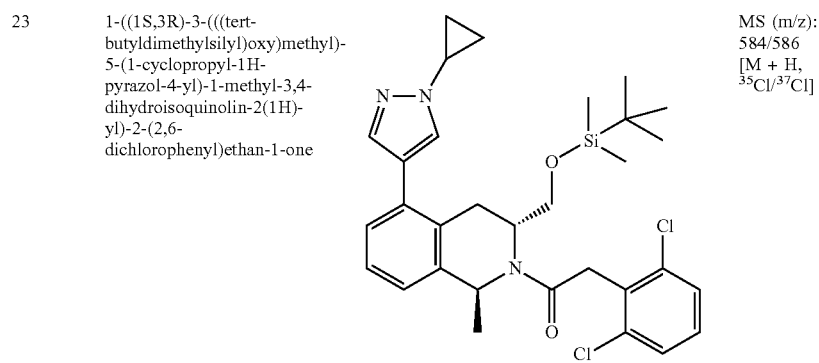 | MS (m/z): 584/586 [M + H, $^{35}$Cl/$^{37}$Cl] |
| 24 | 1-((1S,3R)-3-(((tert-butyldimethylsilyl)oxy)methyl)-1-methyl-5-(1-(oxetan-3-yl)-1H-pyrazol-4-yl)-3,4-dihydroisoquinolin-2(1H)-yl)-2-(2-chloro-6-fluorophenyl)ethan-1-one | 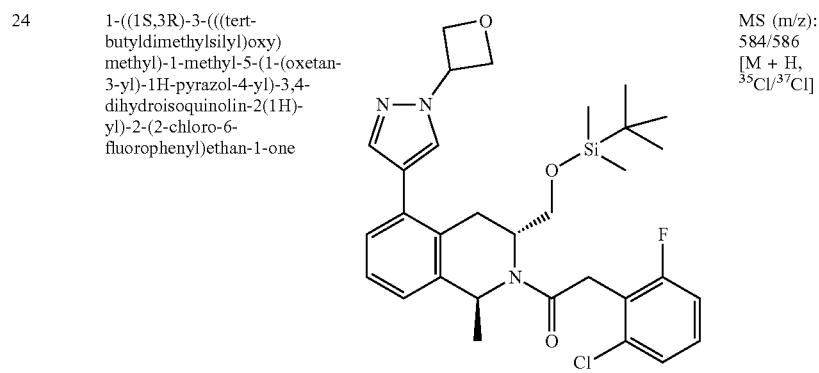 | MS (m/z): 584/586 [M + H, $^{35}$Cl/$^{37}$Cl] |

| Preparation No. | Name | Structure | Physical data |
|---|---|---|---|
| 25 | 1-((1S,3R)-5-(1-(2-(((tert-butyldimethylsilyl)oxy)ethyl)-1H-pyrazol-4-yl)-3-(((tert-butyldimethylsilyl)oxy)methyl)-1-methyl-3,4-dihydroisoquinolin-2(1H)-yl)-2-(2-chlorophenyl)ethan-1-one | 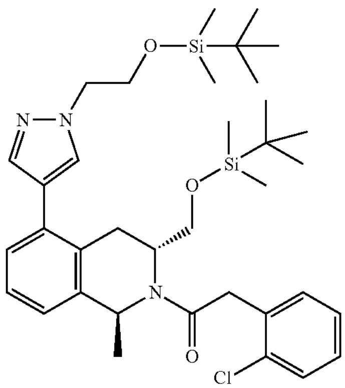 [SMILES: C[C@H]1c2cccc(-c3cnn(CCO[Si](C)(C)C(C)(C)C)c3)c2C[C@H](CO[Si](C)(C)C(C)(C)C)N1C(=O)Cc1ccccc1Cl] | MS (m/z): 668/670 [M + H, $^{35}Cl/^{37}Cl$] |
| 26 | 1-((1S,3R)-3-(((tert-butyldimethylsilyl)oxy)methyl)-1-methyl-5-(1-methyl-1H-pyrazol-4-yl)-3,4-dihydroisoquinolin-2(1H)-yl)-2-(2-chlorophenyl)ethan-1-one | 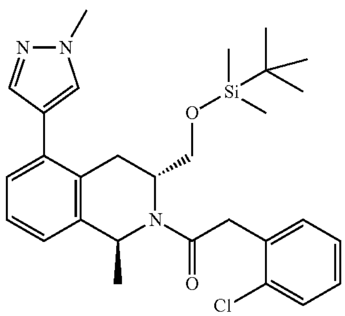 [SMILES: C[C@H]1c2cccc(-c3cnn(C)c3)c2C[C@H](CO[Si](C)(C)C(C)(C)C)N1C(=O)Cc1ccccc1Cl] | MS (m/z): 524/526 [M + H, $^{35}Cl/^{37}Cl$] |

PREPARATION 27

1-(2-((tert-butyldimethylsilyl)oxy)ethyl)-4-(4,4,5,5-tetramethyl-1,3,2-dioxaborolan-2-yl)-1H-pyrazole

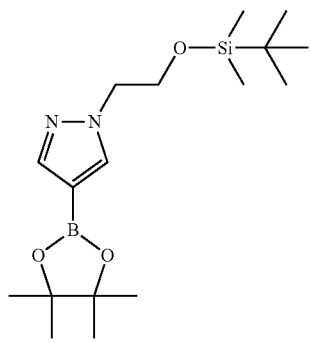 [SMILES: CC1(C)OB(c2cnn(CCO[Si](C)(C)C(C)(C)C)c2)OC1(C)C]

Dissolve 4-(4,4,5,5-tetramethyl-1,3,2-dioxaborolan-2-yl)-1H-pyrazole (1 g, 5.2 mmol) dimethylformamide (20 mL), add cesium carbonate (3.358 g; 10.3 mmol) and (2-bromoethoxy)(tert-butyl)dimethylsilane (1.356 g, 5.7 mmol). Heat to 60° C. for 3 h. Dilute with water, and extract with dichloromethane twice, dry over sodium sulfate, filter, concentrate and purify by silica gel chromatography eluting with a gradient from 0% to 50% EtOAc in hexanes to get the title compound (1.2 g, 67% yield). MS: m/z 353 [M+H].

PREPARATION 28

Benzyl (1S,3R)-5-bromo-3-(((tert-butyldimethylsilyl)oxy)methyl)-1-methyl-3,4-dihydroisoquinoline-2(1H)-carboxylate

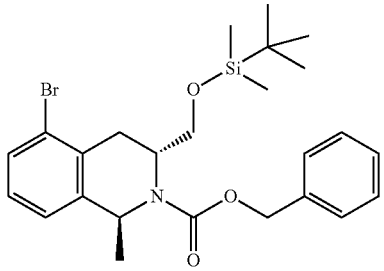 [SMILES: C[C@H]1c2cccc(Br)c2C[C@H](CO[Si](C)(C)C(C)(C)C)N1C(=O)OCc1ccccc1]

Dissolve [(1S,3R)-5-Bromo-1-methyl-1,2,3,4-tetrahydroisoquinolin-3-yl]methoxy-tert-butyl-dimethyl-silane (2.1 g, 5.7 mmol) in acetonitrile (28.5 mL). Add potassium carbonate (2.362 g, 17.089 mmol) and benzyl chloroformate (1 mL, 6.8 mmol). Stir overnight, dilute with saturated aqueous ammonium chloride, and extract with dichloromethane twice, dry over sodium sulfate, filter, concentrate and purify by silica gel chromatography eluting with a gradient from 0% to 50% EtOAc in hexanes to get the title compound (3 g, >99% yield). MS: 504/506 [M+H, $^{79}Br/^{81}Br$)].

PREPARATION 29

Benzyl (1S,3R)-3-(((tert-butyldimethylsilyl)oxy)methyl)-1-methyl-5-(1-(oxetan-3-yl)-1H-pyrazol-4-yl)-3,4-dihydroisoquinoline-2(1H)-carboxylate

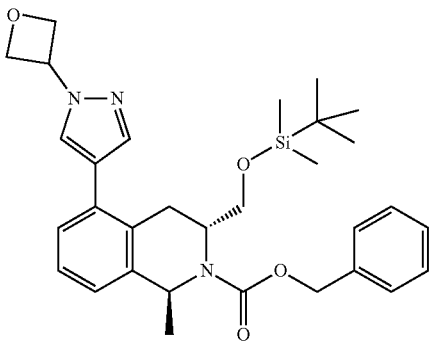 [SMILES: C[C@H]1c2cccc(-c3cnn(C4COC4)c3)c2C[C@H](CO[Si](C)(C)C(C)(C)C)N1C(=O)OCc1ccccc1]

Dissolve benzyl (1S,3R)-5-bromo-3-(((tert-butyldimethylsilyl)oxy)methyl)-1-methyl-3,4-dihydroisoquinoline-2(1H)-carboxylate (500 mg; 1 mmoles) and 1-(oxetan-3-yl)-4-(4,4,5,5-tetramethyl-1,3,2-dioxaborolan-2-yl)-1H-pyrazole (297 mg; 1.2 mmoles) in 1,4-dioxane (9.9 mL). Add a 0.2M aqueous solution of sodium carbonate (5.0 mL, 1 mmol) and bubble nitrogen for 10 min. Add bis(triphenylphosphine)palladium(II) chloride (139 mg, 198 µmoles). Heat to 80° C. for 2 hr. Cool to ambient temperature, dilute with water, extract with EtOAc, dry over sodium sulfate, filter, concentrate and purify by silica gel chromatography eluting with a gradient from 5% to 50% EtOAc in hexanes to get the title compound (180 mg, 33% yield). MS: m/z 548 [M+H].

PREPARATION 30

(1S,3R)-3-(((tert-butyldimethylsilyl)oxy)methyl)-1-methyl-5-(1-(oxetan-3-yl)-1H-pyrazol-4-yl)-1,2,3,4-tetrahydroisoquinoline

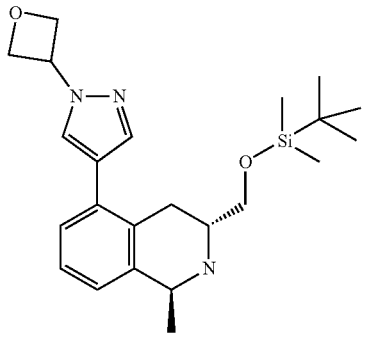 [SMILES: C[C@@H]1N[C@@H](CO[Si](C)(C)C(C)(C)C)Cc2c(-c3cnn(C4COC4)c3)cccc21]

Add benzyl (1S,3R)-3-(((tert-butyldimethylsilyl)oxy)methyl)-1-methyl-5-(1-(oxetan-3-yl)-1H-pyrazol-4-yl)-3,4-dihydroisoquinoline-2(1H)-carboxylate (180 mg 0.3 mmol) and palladium on carbon (17.5 mg, 16.4 µmol) to ethanol (6.5 mL). Stir under a hydrogen balloon for 4 hr. Filter through celite, wash with EtOAc, evaporate to get the crude title compound (140 mg, >99% yield). MS: m/z 414 [M+H].

PREPARATION 31

1-((1S,3R)-3-(((tert-butyldimethylsilyl)oxy)methyl)-1-methyl-5-(1-(oxetan-3-yl)-1H-pyrazol-4-yl)-3,4-dihydroisoquinolin-2(1H)-yl)-2-(2,6-dichlorophenyl)ethan-1-one

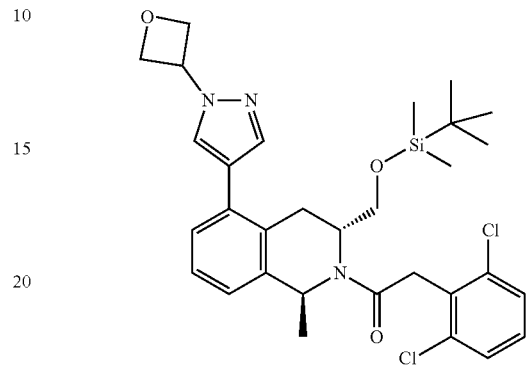

Dissolve (1S,3R)-3-(((tert-butyldimethylsilyl)oxy)methyl)-1-methyl-5-(1-(oxetan-3-yl)-1H-pyrazol-4-yl)-1,2,3,4-tetrahydroisoquinoline (136.5 mg, 0.3 mmol) and 2,6-dichlorophenylacetic acid (74.4 mg, 0.3 mmol) in dichloromethane (3.3 mL). Add O-(7-azabenzotriazol-1-yl)-N,N,N',N'-tetramethyluronium hexafluorophosphate (188.2 mg, 0.5 mmol) and N,N'-diisopropylethylamine (86.32 µL, 0.5 mmol). Stir the resulting mixture for 2 h. Dilute with water, extract twice with dichloromethane, dry over sodium sulfate, filter, concentrate in vacuo, and purify by silica gel chromatography eluting with a gradient from 0% to 50% EtOAc in hexanes to get the title compound (166 mg, 84% yield). MS: m/z 600/602 [M+H, $^{35}Cl/^{37}Cl$].

EXAMPLE 1

2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one

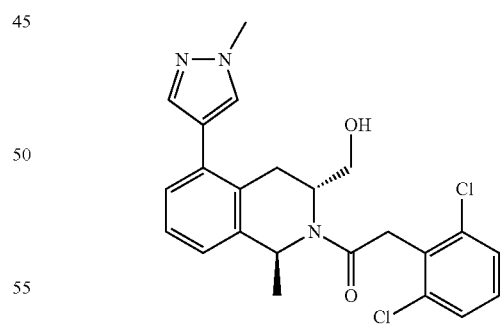

Add tetrabutylammonium fluoride (1M in THF, 0.4 mL) to a solution of 1-[(1S,3R)-3-[(tert-butyl(dimethyl)silyl)oxymethyl]-1-methyl-5-(1-methylpyrazol-4-yl)-3,4-dihydro-1H-isoquinolin-2-yl]-2-(2,6-dichlorophenyl)ethanone (195 mg, 0.3 mmoles) in THF (3.5 mL) at RT. Stir for 4 hr. Quench with saturated aqueous ammonium chloride, extract with EtOAc three times, dry over sodium sulfate, filter, concentrate and purify by silica gel chromatography eluting with a gradient from 0% to 100% EtOAc in hexanes to get the title compound as a white foam (141 mg, 91% yield). MS: m/z 444/446 [M+H, $_{35}C/^{37}Cl$].

The following compounds are prepared essentially by the method of Example 1.

| Example No. | Name | Structure | Physical data |
|---|---|---|---|
| 2 | 2-(2,6-dichlorophenyl)-1-((1S,3R)-5-(1-ethyl-1H-pyrazol-4-yl)-3-(hydroxymethyl)-1-methyl-3,4-dihydroisoquinolin-2(1H)-yl)ethan-1-one | 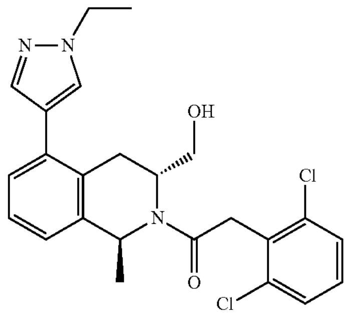 [SMILES: CCn1cc(-c2cccc3c2C[C@H](CO)N(C(=O)Cc2c(Cl)cccc2Cl)[C@H]3C)cn1] | MS (m/z): 458/460 [M + H, $^{35}$Cl/$^{37}$Cl] |
| 3 | 1-((1S,3R)-5-(1-cyclopropyl-1H-pyrazol-4-yl)-3-(hydroxymethyl)-1-methyl-3,4-dihydroisoquinolin-2(1H)-yl)-2-(2,6-dichlorophenyl)ethan-1-one | 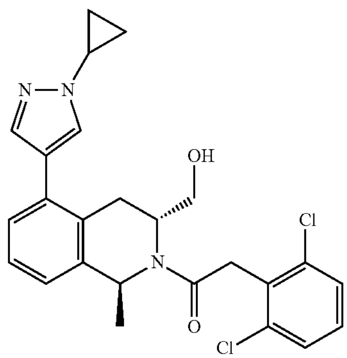 [SMILES: C[C@H]1c2cccc(-c3cnn(C4CC4)c3)c2C[C@H](CO)N1C(=O)Cc1c(Cl)cccc1Cl] | MS (m/z): 470/472 [M + H, $^{35}$Cl/$^{37}$Cl] |
| 4 | 2-(2,6-dichlorophenyl)-1-((1S,3R)-3-(hydroxymethyl)-1-methyl-5-(1-(oxetan-3-yl)-1H-pyrazol-4-yl)-3,4-dihydroisoquinolin-2(1H)-yl)ethan-1-one | 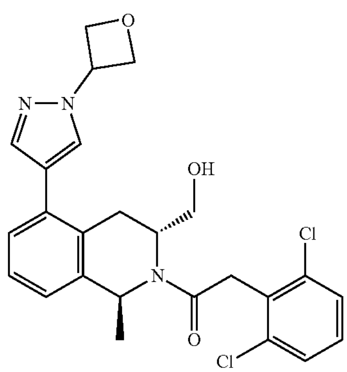 [SMILES: C[C@H]1c2cccc(-c3cnn(C4COC4)c3)c2C[C@H](CO)N1C(=O)Cc1c(Cl)cccc1Cl] | MS (m/z): 486/488 [M + H, $^{35}$Cl/$^{37}$Cl] |
| 5 | 1-((1S,3R)-5-(1-(2-(l1-oxidaneyl)ethyl)-1H-pyrazol-4-yl)-3-(hydroxymethyl)-1-methyl-3,4-dihydroisoquinolin-2(1H)-yl)-2-(2-chlorophenyl)ethan-1-one | 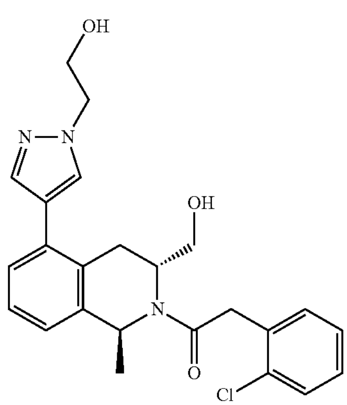 [SMILES: C[C@H]1c2cccc(-c3cnn(CCO)c3)c2C[C@H](CO)N1C(=O)Cc1ccccc1Cl] | MS (m/z): 440/442 [M + H, $^{35}$Cl/$^{37}$Cl] |

| Example No. | Name | Structure | Physical data |
|---|---|---|---|
| 6 | 2-(2-chloro-6-fluorophenyl)-1-((1S,3R)-3-(hydroxymethyl)-1-methyl-5-(1-(oxetan-3-yl)-1H-pyrazol-4-yl)-3,4-dihydroisoquinolin-2(1H)-yl)ethan-1-one | 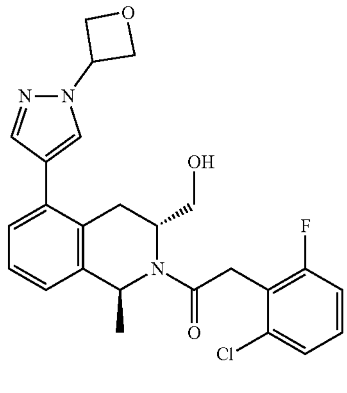 [SMILES: C[C@H]1c2cccc(-c3cnn(C4COC4)c3)c2C[C@H](CO)N1C(=O)Cc1c(F)cccc1Cl] | MS (m/z): 470/472 [M + H, $^{35}Cl/^{37}Cl$] |
| 7 | 2-(2-chlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one | 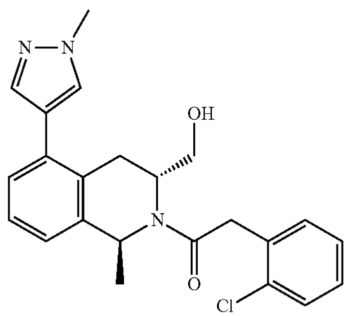 [SMILES: C[C@H]1c2cccc(-c3cnn(C)c3)c2C[C@H](CO)N1C(=O)Cc1ccccc1Cl] | MS (m/z): 410/412 [M + H, $^{35}Cl/^{37}Cl$] |

PREPARATION 32

(R)-5-bromo-3-(((tert-butyldiphenylsilyl)oxy)methyl)-3,4-dihydroisoquinoline, oxalate salt

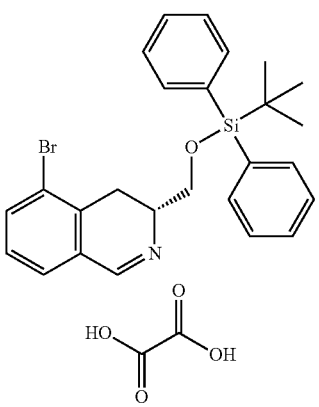

Add (1H)-imidazole (30.7 g, 0.4 mol) to a solution of (3R)-(5-bromo-1,2,3,4-tetrahydroisoquinolin-3-yl)methanol (69.0 g, 0.3 mol) in dichloromethane (459.0 g, 5.4 mol) at room temperature and stir for 20 min. Add tert-butylchlorodiphenylsilane (100.4 g, 0.4 mol) dropwise. Stir at room temperature for 12 hr. Cool to 0° C.

Add triethylamine (100.2 g, 1.0 mol) at 0° C. and stir for 20 minutes. Add N-chlorosuccinimide (60 g, 0.45 mol) portion-wise, maintaining temperature <5° C. and stir at 0° C. for 12 hr. Add aqueous 15% ammonium chloride solution, maintaining temperature <5° C., and stir for 2 hr at 0° C. Extract the organic layer and wash with water twice. Concentrate under reduced pressure and add EtOAc. Add oxalic acid (30.8 g, 0.3 mol) and stir for 10 hr at 40° C. Filter the mixture and wash the solids with EtOAc. Dry the solids at 45° C. for 16 hr to give the title intermediate (131.9 g, 74.6% yield). MS (m/z): 478.0/480 [M+H, $^{7}Br/^{81}Br$].

PREPARATION 33

(1S,3R)-5-bromo-3-(((tert-butyldiphenylsilyl)oxy)methyl)-1-methyl-1,2,3,4-tetrahydroisoquinoline, hemi-sulfate

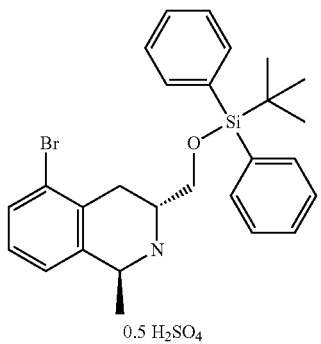 [SMILES: C[C@@H]1N[C@@H](CO[Si](c2ccccc2)(c2ccccc2)C(C)(C)C)Cc2c(Br)cccc21]

Add a potassium carbonate (9.7 g, 70.3 mmol) in water (200 mL) mixture to a solution of (R)-5-bromo-3-(((tert-butyldiphenylsilyl)oxy)methyl)-3,4-dihydroisoquinoline, oxalate salt (20 g, 35.2 mmol) in dichloromethane (280 g, 3.3 mol). Stir at 25° C. for 2 hr. Extract the organic layer and wash with water. Concentrate under reduced pressure and add dry THF (repeat). Add dry THF (360 g, 5.0 mol) and cool to −75° C. Add trimethylsilyl chloride (6 g, 55.0 mmol) and stir for 30 min. Add a 1M solution of methyllithium in THF (77 g, 90.6 mol) portion-wise, maintaining temperature <−70° C. Stir for 6 hr at −75° C. Add saturated ammonium chloride solution slowly, maintaining temperature <0° C. Warm to RT, add water and EtOAc, and stir for 2 hr. Extract the organic layer and wash with water and saturated aqueous NaCl. Concentrate under reduced pressure and add EtOAc (145 g, 1.65 mol). Add concentrated sulfuric acid (1.4 g, 14.3 mmol) portion-wise, and stir at 50° C. for 4 hr. Cool to 20° C. and stir for 16 hr. Filter the mixture and wash the filtercake with EtOAc. Dry the solids at 45° C. for 16 hr. Dissolve solids in THF (63 g, 0.9 mol) and heat to 50° C. Stir for one hr and add EtOAc (108 g) slowly, maintaining temperature between 45-50° C. Stir for 1 hr and cool to 20° C. Stir for 6 hr then filter and collect the solids. Wash the filtercake with EtOAc and dry the solids at 45° C. to give the title intermediate (9.9 g, 57% yield). MS (m/z): 494/496 [M+H, $^{79}$Br/$^{81}$Br].

PREPARATION 34

[(1S,3R)-5-bromo-1-methyl-1,2,3,4-tetrahydroiso-quinolin-3-yl]methoxy-tert-butyl-diphenyl-silane

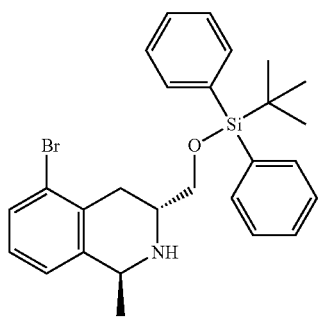 [SMILES: C[C@@H]1N[C@@H](CO[Si](c2ccccc2)(c2ccccc2)C(C)(C)C)Cc2c(Br)cccc21]

Stir a solution of (1S,3R)-5-bromo-3-(((tert-butyldiphenylsilyl)oxy)methyl)-1-methyl-1,2,3,4-tetrahydroisoquinoline, hemi-sulfate (91.0 g, 167.4 mmol) in dichloromethane (700 mL) and add a solution of sodium carbonate (145.5 g, 1373.0 mmol) in water (700 mL) and stir at ambient temperature for 15 min. Separate the layers and extract the aqueous with dichloromethane (250 mL). Combine the organic layers, dry over magnesium sulfate, filter and evaporate to afford the title compound as a yellow-orange oil (86.5 g, 95% yield, of sufficient purity for additional use). MS: m/z 494/496 [M+H, $^{79}$Br/$^{81}$Br].

PREPARATION 35

1-[(1S,3R)-5-Bromo-3-[[tert-butyl(diphenyl)silyl]oxymethyl]-1-methyl-3,4-dihydro-1H-isoquinolin-2-yl]-2-(2,6-dichlorophenyl)ethanone

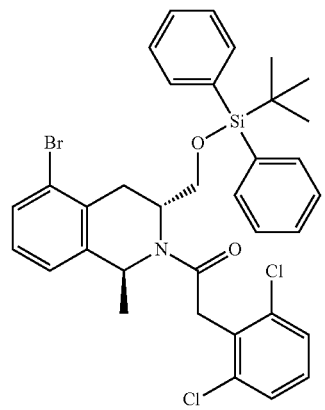 [SMILES: C[C@H]1c2cccc(Br)c2C[C@H](CO[Si](c2ccccc2)(c2ccccc2)C(C)(C)C)N1C(=O)Cc1c(Cl)cccc1Cl]

Dissolve [(1S,3R)-5-bromo-1-methyl-1,2,3,4-tetrahydroisoquinolin-3-yl]methoxy-tert-butyl-diphenyl-silane (86.5 g, 159.1 mmol) in acetonitrile (750 mL) and add trimethylamine (50 mL, 359 mmol) and 2-(2,6-dichlorophenyl)acetic acid (38.4 g, 187.0 mmol), and stir the mixture for 5 min. Cool the mixture at 5 and 10° C. In a separate vessel, dilute a 50% solution of 1-propanephosphonic anhydride in EtOAc (103 mL, 173.0 mmol) with acetonitrile (85 mL) and add dropwise to the reaction mixture over 15 min, maintaining the internal temperature below 10° C. Stir between 5-10° C. for 1 hr, and warm to ambient temperature. Filter the mixture and wash the resulting filtercake with acetonitrile (2×150 mL) and dry under vacuum at 45° C. overnight to afford the title intermediate (100.5 g, 93% yield) MS: m/z 680/682/684 [M+H, $^{35}$Cl/$^{37}$Cl/$^{79}$Br/$^{81}$Br)].

PREPARATION 36

1-[(1S,3R)-3-[[tert-butyl(diphenyl)silyl]oxymethyl]-1-methyl-5-(1-methylpyrazol-4-yl)-3,4-dihydro-1H-isoquinolin-2-yl]-2-(2,6-dichlorophenyl)ethanone

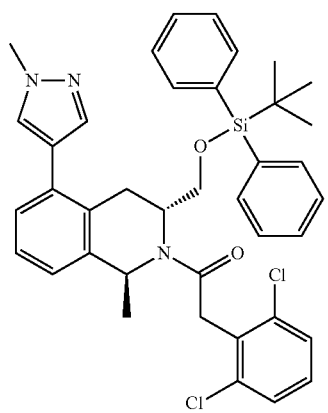 [SMILES: C[C@H]1c2cccc(-c3cnn(C)c3)c2C[C@H](CO[Si](c2ccccc2)(c2ccccc2)C(C)(C)C)N1C(=O)Cc1c(Cl)cccc1Cl]

Add 1-[(1S,3R)-5-bromo-3-[[tert-butyl(diphenyl)silyl]oxymethyl]-1-methyl-3,4-dihydro-1H-isoquinolin-2-yl]-2-(2,6-dichlorophenyl)ethanone (60.3 g, 83.2 mmol), 1-methyl-4-(4,4,5,5-tetramethyl-1,3,2-dioxaborolan-2-yl)pyrazole (20.7 g, 99.5 mmol), sodium carbonate (26.4 g, 249 mmol), bis(triphenylphosphine)palladium(II) dichloride (1.2 g, 1.7 mmol) to a three-necked 2 L flask, and seal and purge the reaction system with vacuum/nitrogen cycle three times. Add 1,4-dioxane (550 mL) and water (300 mL), and degas with further vacuum/nitrogen cycling three times, and heat the resulting mixture to 80° C. for 75 min. Add 1-methyl-4-(4,4,5,5-tetramethyl-1,3,2-dioxaborolan-2-yl)pyrazole (5.0 g, 24.0 mmol) and bis(triphenylphosphine)palladium(II) dichloride (580 mg, 0.8 mmol). Seal and purge with vacuum/nitrogen cycle three times, and heat to 80° C. for another 75 min. Cool to RT, dilute with EtOAc (500 mL), separate layers, and pass the organic layer through a plug of silica gel to afford the crude title compound as an orange oil (99.67 g of sufficient purity for additional use). MS: m/z 682/684 [M+H, $^{35}Cl/^{37}Cl$].

ALTERNATIVE PROCEDURE FOR EXAMPLE 1

2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one Dissolve 1-[(1S,3R)-3-[[tert-butyl(diphenyl)silyl]oxymethyl]-1-methyl-5-(1-methylpyrazol-4-yl)-3,4-dihydro-1H-isoquinolin-2-yl]-2-(2,6-dichlorophenyl)ethanone (99.67 g, 103.6 mmol) in 2-methyltetrahydrofuran (1 L) and placed under a nitrogen atmosphere in a 2 L flask. Add a 1M solution of tetrabutylammonium fluoride in THF (155 mL, 155 mmol) over 2 min, and stir at RT for 4 hr. Dilute with water (500 mL), and separate the organic layer. Dry over magnesium sulfate, filter, and concentrate in vacuo to afford a pale orange oil. Purify the resulting residue by silica gel chromatography, eluting with heptane (2 L), heptane/EtOAc (1:1, 4 L), and EtOAc (6 L), to afford the title compound as a white foam (33 g). Purify again by silica gel chromatography eluting with a gradient from 0% to 50% MTBE in dichloromethane to afford the title compound as a white foam (28.6 g, 61% yield). MS: m/z 444/446 [M+H, $^{35}Cl/^{37}Cl$].

PREPARATION 37

1-((1S,3R)-3-(((tert-butyldimethylsilyl)oxy)methyl)-1-methyl-5-(1H-pyrazol-4-yl)-3,4-dihydroisoquinolin-2(1H)-yl)-2-(2,6-dichlorophenyl)ethan-1-one

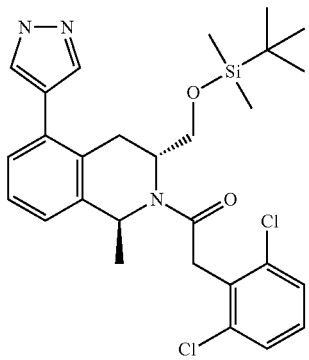 [SMILES: C[C@H]1c2cccc(-c3cn[nH]c3)c2C[C@H](CO[Si](C)(C)C(C)(C)C)N1C(=O)Cc1c(Cl)cccc1Cl]

Dissolve 1-((1S,3R)-5-bromo-3-(((tert-butyldimethylsilyl)oxy)methyl)-1-methyl-3,4-dihydroisoquinolin-2(1H)-yl)-2-(2,6-dichlorophenyl)ethan-1-one (2.0 g; 3.6 mmoles) and 4-(4,4,5,5-tetramethyl-1,3,2-dioxaborolan-2-yl)-1H-pyrazole (1.74 g; 9.0 mmoles) in 1,2-dimethoxyethane (36 mL). Add a 0.2M aqueous solution of potassium carbonate (17.9 mL, 0.4 mmol) and bubble nitrogen for 10 min. Add tetrakis(triphenylphosphine)palladium (414.0 mg, 359.0 μmoles). Heat to 100° C. for 18 h. Cool to RT, dilute with water, extract with EtOAc, dry over sodium sulfate, filter, concentrate in vacuo, and purify by silica gel chromatography eluting with a gradient from 2% to 80% EtOAc in hexanes to provide the title compound (750 mg 38% yield). MS: m/z 544/546 [M+H, $^{35}Cl/^{37}Cl$].

EXAMPLE 8

2-(2,6-dichlorophenyl)-1-((1S,3R)-3-(hydroxymethyl)-1-methyl-5-(1H-pyrazol-4-yl)-3,4-dihydroisoquinolin-2(1H)-yl)ethan-1-one

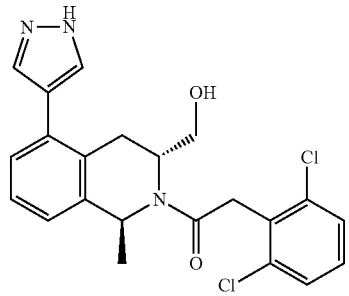

Add a 1M solution of tetrabutylammonium fluoride in THF (1.5 mL, 1.5 mmol) to a solution of 1-((1S,3R)-3-(((tert-butyldimethylsilyl)oxy)methyl)-1-methyl-5-(1H-pyrazol-4-yl)-3,4-dihydroisoquinolin-2(1H)-yl)-2-(2,6-dichlorophenyl)ethan-1-one (750 mg, 1.4 mmoles) in THF (13.8 mL) at RT. Stir the resulting mixture for 3 hrs. Quench with saturated aqueous ammonium chloride, extract three times with EtOAc, dry over sodium sulfate, filter, concentrate in vacuo, and purify the resulting residue by silica gel chromatography eluting with a gradient from 0% to 100% EtOAc in hexanes to get the title compound as a white foam (560 mg, 83% yield). MS: m/z 430/432 [M+H, $^{35}Cl/^{37}Cl$].

ALTERNATIVE SYNTHESIS OF EXAMPLE 8

Preparation 38

1-((1S,3R)-3-(((tert-butyldimethylsilyl)oxy)methyl)-1-methyl-5-(1-(tetrahydro-2H-pyran-2-yl)-1H-pyrazol-4-yl)-3,4-dihydroisoquinolin-2(1H)-yl)-2-(2,6-dichlorophenyl)ethan-1-one

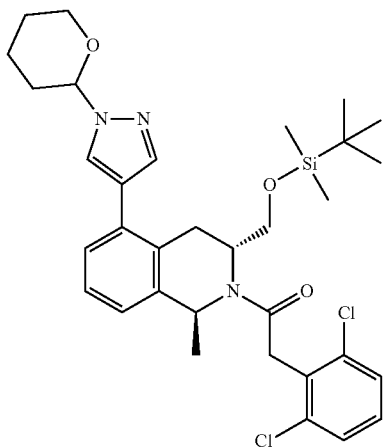 [SMILES: C[C@H]1c2cccc(-c3cnn(C4CCCCO4)c3)c2C[C@H](CO[Si](C)(C)C(C)(C)C)N1C(=O)Cc1c(Cl)cccc1Cl]

Dissolve 1-((1S,3R)-5-bromo-3-(((tert-butyldimethylsilyl)oxy)methyl)-1-methyl-3,4-dihydroisoquinolin-2(1H)-yl)-2-(2,6-dichlorophenyl)ethan-1-one (4.2 g; 7.5 mmoles) and (1-tetrahydropyran-2-ylpyrazol-4-yl)boronic acid (2.2 g; 11.3 mmoles) in 1,4-dioxane (63 mL). Add sodium carbonate (1.6 g, 15.1 mmol), (1,1'-bis(diphenylphosphino)ferrocene)palladium(II) chloride (307 mg, 0.4 mmol) and water (21 mL). Bubble nitrogen for 5 min. Heat to 90° C. for 19 hr. Cool to RT, dilute with water, extract with EtOAc, dry over sodium sulfate, filter, concentrate in vacuo, and purify by silica gel chromatography eluting with 3:7 EtOAc/heptane to get the title compound (2.98 g, 63% yield). MS: m/z 628/630 [M+H, $^{35}C/^{37}Cl$].

2-(2,6-dichlorophenyl)-1-((1S,3R)-3-(hydroxymethyl)-1-methyl-5-(1H-pyrazol-4-yl)-3,4-dihydroisoquinolin-2(1H)-yl)ethan-1-one Add portion-wise over 10 min 10-camphorsulfonic acid (3.2 g, 13.4 mmol) to a solution of 1-((1S,3R)-3-(((tert-butyldimethylsilyl)oxy)methyl)-1-methyl-5-(1H-pyrazol-4-yl)-3,4-dihydroisoquinolin-2(1H)-yl)-2-(2,6-dichlorophenyl)ethan-1-one (3.8 g, 6.1 mmoles) in MeOH (38.2 mL) at RT. Stir for 17 hr. Remove solvent under vacuum, partition the resulting residue between EtOAc (50 mL) and water (50 mL), separate the layers, and extract the aqueous layer twice with EtOAc. Dry the combined organic extracts over MgSO$_4$, filter, concentrate in vacuo, and purify by silica gel chromatography eluting with a gradient from 20% to 100% EtOAc in hexanes to get the title compound as a white foam (1.72 g, 66% yield). MS: m/z 430/432 [M+H, $^{35}Cl/^{37}Cl$].

EXAMPLE 9

2-(2-chloro-6-fluorophenyl)-1-((1S,3R)-3-(hydroxymethyl)-1-methyl-5-(1H-pyrazol-4-yl)-3,4-dihydroisoquinolin-2(1H)-yl)ethan-1-one

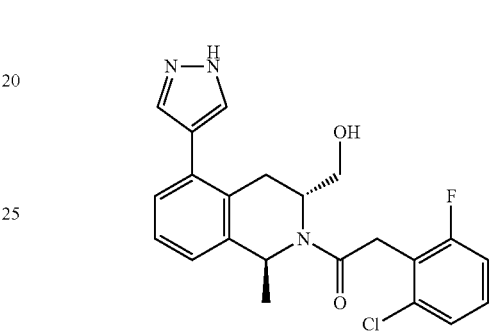

Heat a mixture of potassium carbonate (92 mg, 0.7 mmol), 1-(tetrahydro-2H-pyran-2-yl)-4-(4,4,5,5-tetramethyl-1,3,2-dioxaborolan-2-yl)-1H-pyrazole (160.0 mg, 0.4 mmol), 1,1'-bis(di-t-butylphosphino)ferrocene palladium dichloride (11.6 mg, 20 μmol), 1-[(1S,3R)-5-bromo-3-[[tert-butyl(dimethyl)silyl]oxymethyl]-1-methyl-3,4-dihydro-1H-isoquinolin-2-yl]-2-(2-chloro-6-fluoro-phenyl)ethanone (240.0 mg, 0.4 mmol), THF (1.5 mL), and water (1.0 mL) in a microwave reactor at 100° C. for 1 hr. Cool to RT, dilute with water, extract with EtOAc, and concentrate in vacuo to obtain a crude brown residue. Dissolve the residue in methanol (6 mL) and add 1.25M aqueous HCl solution in methanol (2.8 mL, 3.5 mmol). Heat the resulting solution to 50° C. for 8 hrs. Cool to RT, and pour over an SCX column first eluting with methanol and eluting the desired product with 2N ammonia in methanol. Concentrate the methanolic ammonia fractions and purify by reversed-phase chromatography to give the title compound (40 mg, 24% yield) MS (m/z): 414/414 [M+H, $^{35}Cl/^{37}Cl$]

The following compounds are prepared essentially by the method of Example 9.

| Example No. | Name | Structure | Physical data |
|---|---|---|---|
| 10 | 2-(2,6-difluorophenyl)-1-((1S,3R)-3-(hydroxymethyl)-1-methyl-5-(1H-pyrazol-4-yl)-3,4-dihydroisoquinolin-2(1H)-yl)ethan-1-one | 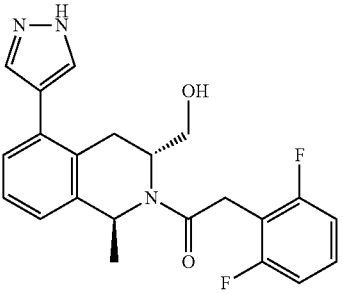 [SMILES: C[C@H]1c2cccc(-c3cn[nH]c3)c2C[C@H](CO)N1C(=O)Cc1c(F)cccc1F] | MS (m/z): 398/400 [M + H] |

-continued

| Example No. | Name | Structure | Physical data |
|---|---|---|---|
| 11 | 2-(2-chloro-5-fluorophenyl)-1-((1S,3R)-3-(hydroxymethyl)-1-methyl-5-(1H-pyrazol-4-yl)-3,4-dihydroisoquinolin-2(1H)-yl)ethan-1-one | 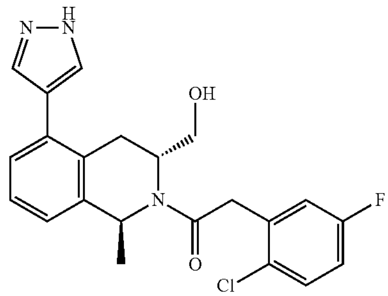 [SMILES: C[C@H]1c2cccc(-c3cn[nH]c3)c2C[C@H](CO)N1C(=O)Cc1cc(F)ccc1Cl] | MS (m/z): 414/416 [M + H] |
| 12 | 2-(2-chloro-4-fluorophenyl)-1-((1S,3R)-3-(hydroxymethyl)-1-methyl-5-(1H-pyrazol-4-yl)-3,4-dihydroisoquinolin-2(1H)-yl)ethan-1-one | 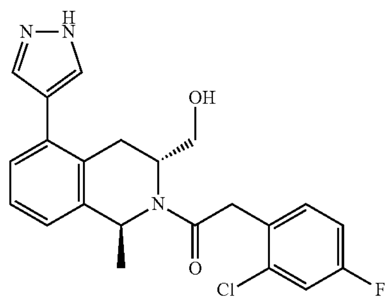 [SMILES: C[C@H]1c2cccc(-c3cn[nH]c3)c2C[C@H](CO)N1C(=O)Cc1ccc(F)cc1Cl] | MS (m/z): 414/416 [M + H] |
| 13 | 2-(2-fluorophenyl)-1-((1S,3R)-3-(hydroxymethyl)-1-methyl-5-(1H-pyrazol-4-yl)-3,4-dihydroisoquinolin-2(1H)-yl)ethan-1-one | 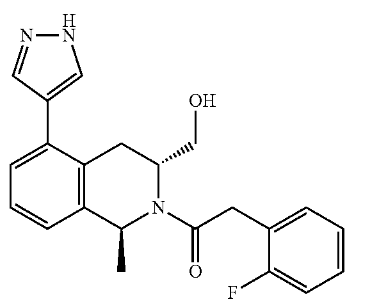 [SMILES: C[C@H]1c2cccc(-c3cn[nH]c3)c2C[C@H](CO)N1C(=O)Cc1ccccc1F] | MS (m/z): 380 [M + H] |
| 14 | 2-(2,3-difluorophenyl)-1-((1S,3R)-3-(hydroxymethyl)-1-methyl-5-(1H-pyrazol-4-yl)-3,4-dihydroisoquinolin-2(1H)-yl)ethan-1-one | 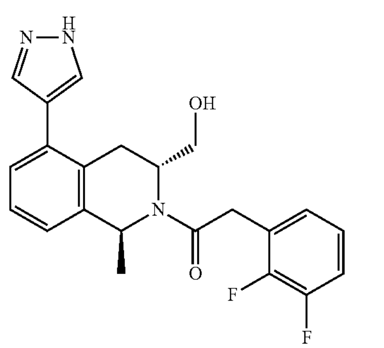 [SMILES: C[C@H]1c2cccc(-c3cn[nH]c3)c2C[C@H](CO)N1C(=O)Cc1cccc(F)c1F] | MS (m/z): 398 [M + H] |
| 15 | 2-(2,5-difluorophenyl)-1-((1S,3R)-3-(hydroxymethyl)-1-methyl-5-(1H-pyrazol-4-yl)-3,4-dihydroisoquinolin-2(1H)-yl)ethan-1-one | 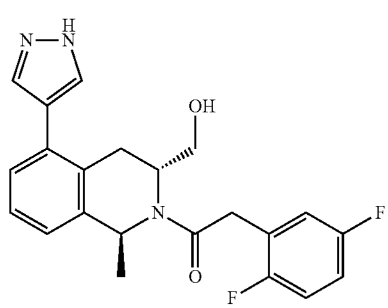 [SMILES: C[C@H]1c2cccc(-c3cn[nH]c3)c2C[C@H](CO)N1C(=O)Cc1cc(F)ccc1F] | MS (m/z): 398 [M + H] |

PREPARATION OF EXAMPLE 1A 2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one hydrochloride monohydrate The compound of Example 1 (2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one, 412 mg, 0.9 mmol) is dissolved in acetone (5 mL) at 60° C./1000 rpm. A 1M solution of HCl in EtOAc (1 mL) is added dropwise. A white solid precipitates after addition, resulting in a thick white slurry. The resulting white solid is isolated by filtration on Whatman paper and dried under air stream for 30 min to yield the title compound (400 mg recovered, 86.5% yield) as a crystalline solid.

PREPARATION OF EXAMPLE 1B 2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one hydrobromide The compound of Example 1 (2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one, 432.6 g, 563 mmol) is dissolved in acetone (6 L) at 55° C. Once internal temperature reaches at 50° C., a 48% aqueous solution of HBr (70 mL, 619 mmol) is added. After 2 mins a precipitate forms, and the mixture is stirred for 10 min and cooled to RT. The resulting precipitate is collected by filtration over a sintered glass filter, washed with acetone (~1.5 L), and dried by vacuum suction on the sinter, to give the title compound (271.2 g, 91% yield) as a light peach-colored crystalline solid.

PREPARATION OF EXAMPLE 1C 2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one hydrobromide monohydrate The compound of Example 1 (2.6 g, 5.8 mmol) is dissolved in acetone (20 mL) at 60° C./1000 rpm. A mixture of 48% aqueous HBr diluted 1:9 in acetone (8 mL) is added at 500 µL/min. A white solid starts to precipitate after addition of 1 mL. After the acid addition, a thick white slurry results and the mixture is cooled to RT. The white solid is collected by filtration on Whatman paper and dried under air stream for 90 min to obtain the title compound (2.9 g, 91% yield) as a crystalline solid.

The present invention provides crystalline 2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one hydrobromide monohydrate. An embodiment of the invention is crystalline 2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one hydrobromide monohydrate characterized by an X ray powder diffraction pattern using CuKα radiation having a diffraction peak at diffraction angle 2-theta of 17.4 in combination with one or more of the peaks selected from the group consisting of 27.0, 18.3, and 21.7; with a tolerance for the diffraction angles of 0.2 degrees. The present invention further provides a pharmaceutical composition comprising 2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one hydrobromide monohydrate, and a pharmaceutically acceptable carrier, diluent or excipient. The present invention further provides a pharmaceutical composition comprising crystalline 2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one hydrobromide monohydrate, and a pharmaceutically acceptable carrier, diluent or excipient.

PREPARATION OF EXAMPLE 1D 2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one hydroiodide The compound of Example 1 (166 mg, 0.37 mmol) is dissolved in acetone (3 mL) at RT/1000 rpm. An aqueous solution of 57% HI (60 µL) is added. The mixture is stirred for 1 h, and a white solid precipitates out of solution, forming a thick slurry of white solid in brown supernatant. The white solid is collected by filtration on Whatman paper and dried under air stream for 10 min to obtain the title compound (158 mg, 74% yield) as a crystalline solid.

PREPARATION OF EXAMPLE 1E 2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one hydroiodide monohydrate The compound of Example 1 (2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one, 209.6 mg, 0.47 mmol) is dissolved in acetone (3 mL) at RT/1000 rpm. An aqueous solution of 57% HI (80 µL) is added. The mixture is stirred for 30 min, and a white solid precipitates out of solution, forming a thick slurry of white solid in brown supernatant. The white solid is collected by filtration on Whatman paper and dried under air stream for 10 min to obtain the title compound (262 mg, 94% yield) as a crystalline solid.

X-Ray Powder Diffraction of Crystalline Forms

The XRD patterns of crystalline solids are obtained on a Bruker D4 Endeavor X-ray powder diffractometer, equipped with a CuKa source, λ=1.54060 Å) and a Vantec detector, operating at 35 kV and 50 mA. The sample is scanned between 4 and 40° in 2θ, with a step size of 0.0080 in 2θ and a scan rate of 0.5 seconds/step, and with 1.0 mm divergence, 6.6 fixed anti-scatter, and 11.3 mm detector slits. The dry powder is packed on a quartz sample holder and a smooth surface is obtained using a glass slide. The crystal form diffraction patterns are collected at ambient temperature and relative humidity. Crystal peak positions are determined in MDI-Jade after whole pattern shifting based on an internal NIST 675 standard with peaks at 8.853 and 26.774 2θ. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature at which a sample is analyzed, sample displacement, or the presence or absence of an internal standard. In the present case, a peak position variability of 0.2 2θ° is presumed to take into account these potential variations without hindering the unequivocal identification of the indicated crystal form. Confirmation of a crystal form may be made based on any unique combination of distinguishing peaks.

XRD OF EXAMPLE 1A

A prepared sample of crystalline Example 1A (2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one hydrochloride monohydrate) is characterized by an XRD pattern using CuKa radiation as having diffraction peaks (2-theta values) as described in Table 1 below, and in particular having peaks at 8.6 in combination with one or more of the peaks selected from the group consisting of 15.3, 17.5, and 28.3; with a tolerance for the diffraction angles of 0.2 degrees.

TABLE 1

X-ray powder diffraction peaks of the crystalline Example 1A

| Peak | Angle (°2-Theta) +/− 0.2° | Relative Intensity (% of most intense peak) |
|---|---|---|
| 1 | 8.6 | 100.0% |
| 2 | 9.3 | 40.2% |
| 3 | 14.6 | 50.3% |
| 4 | 15.3 | 69.3% |
| 5 | 17.5 | 68.9% |
| 6 | 19.1 | 23.3% |
| 7 | 22.5 | 36.1% |
| 8 | 23.9 | 34.1% |
| 9 | 25.4 | 22.9% |
| 10 | 28.3 | 57.3% |

XRD OF EXAMPLE 1B

A prepared sample of the crystalline Example 1B (2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one hydrobromide) is characterized by an XRD pattern using CuKa radiation as having diffraction peaks (2-theta values) as described in Table 2 below, and in particular having peaks at 15.5 in combination with one or more of the peaks selected from the group consisting of 24.9, 11.9, and 21.5; with a tolerance for the diffraction angles of 0.2 degrees.

TABLE 2

X-ray powder diffraction peaks of the crystalline Example 1B

| Peak | Angle (°2-Theta) +/− 0.2° | Relative Intensity (% of most intense peak) |
|---|---|---|
| 1 | 11.9 | 69.3% |
| 2 | 12.7 | 55.7% |
| 3 | 15.5 | 100.0% |
| 4 | 16.8 | 50.3% |
| 5 | 17.9 | 47.7% |
| 6 | 19.1 | 38.4% |

TABLE 2-continued

X-ray powder diffraction peaks of the crystalline Example 1B

| Peak | Angle (°2-Theta) +/− 0.2° | Relative Intensity (% of most intense peak) |
|---|---|---|
| 7 | 19.6 | 46.6% |
| 8 | 21.5 | 65.8% |
| 9 | 24.9 | 92.1% |
| 10 | 27.7 | 31.2% |

XRD OF EXAMPLE 1C

A prepared sample of the crystalline Example 1C (2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one hydrobromide monohydrate) is characterized by an XRD pattern using CuKa radiation as having diffraction peaks (2-theta values) as described in Table 3 below, and in particular having peaks at 17.4 in combination with one or more of the peaks selected from the group consisting of 27.0, 18.3, and 21.7; with a tolerance for the diffraction angles of 0.2 degrees.

TABLE 3

X-ray powder diffraction peaks of the crystalline Example 1C

| Peak | Angle (°2-Theta) +/− 0.2° | Relative Intensity (% of most intense peak) |
|---|---|---|
| 1 | 8.4 | 26.9% |
| 2 | 11.5 | 23.6% |
| 3 | 14.1 | 19.5% |
| 4 | 16.8 | 30.8% |
| 5 | 17.4 | 100.0% |
| 6 | 18.3 | 52.1% |
| 7 | 19.7 | 37.2% |
| 8 | 21.7 | 39.7% |
| 9 | 23.1 | 37.8% |
| 10 | 27.0 | 65.5% |

XRD OF EXAMPLE 1D

A prepared sample of the crystalline Example 1D (2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one hydroiodide) is characterized by an XRD pattern using CuKa radiation as having diffraction peaks (2-theta values) as described in Table 4 below, and in particular having peaks at 15.3 in combination with one or more of the peaks selected from the group consisting of 21.5, 11.7, and 24.5; with a tolerance for the diffraction angles of 0.2 degrees.

TABLE 4

X-ray powder diffraction peaks of the crystalline Example 1D

| Peak | Angle (°2-Theta) +/− 0.2° | Relative Intensity (% of most intense peak) |
|---|---|---|
| 1 | 11.7 | 45.2% |
| 2 | 15.3 | 100.0% |
| 3 | 17.9 | 18.3% |
| 4 | 19.1 | 21.1% |
| 5 | 19.6 | 22.6% |
| 6 | 20.2 | 32.0% |
| 7 | 21.3 | 37.2% |
| 8 | 21.5 | 46.1% |

TABLE 4-continued

X-ray powder diffraction peaks of the crystalline Example 1D

| Peak | Angle (°2-Theta) +/- 0.2° | Relative Intensity (% of most intense peak) |
|---|---|---|
| 9 | 21.9 | 39.7% |
| 10 | 24.5 | 40.3% |

XRD OF EXAMPLE 1E

A prepared sample of the crystalline Example 1E (2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one hydroiodide monohydrate) is characterized by an XRD pattern using CuKa radiation as having diffraction peaks (2-theta values) as described in Table 5 below, and in particular having peaks at 17.2 in combination with one or more of the peaks selected from the group consisting of 21.5, 19.6, and 28.1; with a tolerance for the diffraction angles of 0.2 degrees.

TABLE 5

X-ray powder diffraction peaks of the crystalline Example 1E

| Peak | Angle (°2-Theta) +/- 0.2° | Relative Intensity (% of most intense peak) |
|---|---|---|
| 1 | 11.4 | 16.5% |
| 2 | 14.5 | 8.9% |
| 3 | 16.7 | 25.7% |
| 4 | 17.2 | 100.0% |
| 5 | 17.8 | 11.3% |
| 6 | 18.2 | 20.7% |
| 7 | 19.6 | 33.7% |
| 8 | 21.5 | 36.2% |
| 9 | 25.1 | 20.5% |
| 10 | 28.1 | 31.7% |

Human D1 Receptor PAM Assay

The PAM activity of the compounds of the present invention may be measured essentially as described in Svensson et al., An Allosteric Potentiator of the Dopamine D1 Receptor Increases Locomotor Activity in Human D1 Knock-in Mices without Casusing Stereotypy or Tachyphylaxis. *J. Pharmacol. Exp. Ther.* (2017) 360:117-128.

More specifically, HEK293 cells that stably express the human D1 receptor (Accession number NM_000794) are generated by gene transduction using the pBABE-bleo retroviral vector and selected with Zeocin™ (InvivoGen). At approximately 80% confluency, the cells are harvested using TrypLE™ Express (Gibco), suspended in FBS plus 8% DMSO, and stored in liquid nitrogen. On the day of the assay, cells are thawed and resuspended in STIM buffer (Hanks Balanced Salt Solution supplemented with 0.1% BSA, 20 mM HEPES, 500 µM IBMX, and 100 µM ascorbic acid).

Test compound is serially diluted (1:2) with DMSO into assay plates (ProxiPlate-384 Plus, PerkinElmer) using acoustic dispensing (Labcyte) to provide 20 concentrations for full response curves. Test compound (80 nL) is added to 5 µL STIM buffer containing 2000 cells, and 5 µL of a 2× concentration dopamine solution in STIM buffer that will generate an $EC_{20}$ level response (24 nM in stock solution, or 12 nM final) and a final DMSO concentration in the well of 0.8%. Plates are incubated at room temperature for a total reaction time of 60 min.

cAMP production is quantified using HTRF® detection (Cisbio) according to the manufacturer's instructions. Generally, lysis buffer containing anti-cAMP cryptate (5 µL) and D2-conjugate (from HTRF® kit) (5 µL) is added to the wells, plates are incubated for an additional 60-90 min, and the time-resolved fluorescence is detected using an EnVision™ plate reader (PerkinElmer). Fluorescence data is converted to cAMP concentrations using a cAMP standard curve and analyzing using a 4-parameter non-linear logistic equation (Genedata Screener, version 13.0.5-standard). For potentiator mode concentration-response curves, results are expressed as percent of the window between a response at $EC_{20}$ concentration of dopamine alone (normalized to 0%) and the maximum response to dopamine (defined by response to 5 µM dopamine, final concentration, normalized as 100%).

Absolute $EC_{50}$ values are calculated based on the maximum and minimum responses of the control agonist (dopamine). The % Potentiation (% Top) is determined from the fitted top of the concentration response curve. The absolute $EC_{50}$ and % Top are showed in the following Table 6:

TABLE 6

| Example No. | Abs $EC_{50}$ (nM) (SEM, N) | % Top (SEM, N) |
|---|---|---|
| 1 | 16.4 (3.18, n = 10) | 91.4 (3.65, n = 10) |
| 2 | 172 (29.5, n = 3) | 91.2 (6.46, n = 3) |
| 3 | 287 (38.1, n = 3) | 88.1 (2.52, n = 3) |
| 4 | 28.5 (5.45, n = 3) | 78.8 (4.86, n = 3) |
| 5 | 18.3 (2.62, n = 3) | 79.1 (4.34, n = 3) |
| 6 | 42.2 (3.70, n = 3) | 80.4 (3.40, n = 3) |
| 7 | 81.2 (11.6, n = 3) | 82.4 (2.83, n = 3) |
| 8 | 13.4 (3.93, n = 3) | 75.9 (3.16, n = 3) |
| 9 | 28.0 (6.81, n = 3) | 81.5 (3.16, n = 3) |
| 10 | 127 (24.8, n = 3) | 78.1 (4.68, n = 3) |
| 11 | 112 (13.8, n = 3) | 79.8 (3.10, n = 3) |
| 12 | 540 (41.6, n = 3) | 77.1 (2.50, n = 3) |
| 13 | 484 (14.9, n = 2) | 89.8 (2.42, n = 2) |
| 14 | 677 (23.9, n = 2) | 72.6 (3.38, n = 2) |
| 15 | 836 (46.4, n = 2) | 75.5 (0.226, n = 2) |

The absolute $EC_{50}$ values provided for Examples 1-15 in Table 6 illustrate the potentiation of human D1 receptor signaling in response to dopamine, and illustrate the activity of the compounds of Claim 1 as a positive allosteric modulator of the human dopamine D1 receptor.

Generation of Human D1 Receptor Knock-in Mouse

A transgenic mouse in which the murine dopamine 1 (D1) receptor is replaced by its human counterpart may be generated by standard techniques (see generally Svensson et al., *J. Pharmacol. Exp. Ther.* (2017) 360:117-128). For example, mouse genomic fragments are subcloned from the RP23 bacterial artificial chromosome library and recloned into a PGK-neo targeting vector. The mouse open reading frame is replaced with the human D1 receptor open reading frame in exon 2. A neo selection marker upstream of exon 2 is flanked by frt sites for later removal. The flanking of exon 2 by loxP selection sites allows for the option to generate D1 knock-out mice by crossing with mice expressing the cre nuclease gene.

The C57BL/6 N embryonic stem cell line B6-3 is grown on a mitotically inactivated feeder layer of mouse embryonic fibroblasts in high-glucose DMEM with 20% FBS and $2 \times 10^6$ unit/i leukemia inhibitory factor. Ten million embryonic stem cells plus 30 micrograms of linearized vector DNA are electroporated and subjected to G418 selection (200 µg/ml). Clones are isolated and analyzed by Southern blotting.

A clone containing the expected size insert is inserted into blastocysts and the resulting mice are genotyped by PCR. A male chimera is crossed with a female containing the flp nuclease gene to eliminate the selection marker. Progeny containing the human D1 receptor without the selection marker are identified by PCR. A male heterozygote is mated with female C57BL/6 mice. Male and female progeny containing the human D1 receptor are mated and homozygotes are identified by PCR. Behavior and reproduction of the homozygotes is found to be normal, and the colony is maintained in the homozygote state for succeeding generations.

Basal (Habituated) Locomotor Activity

The in vivo efficacy of the present compounds may be demonstrated to act through the D1 receptor using mouse locomotor activity. Locomotor activity is measured using an automated system to track movement in mice. Monitoring of mouse locomotor activity behaviors take place in transparent plastic shoebox cages having dimensions of 45×25×20 cm, with a 1 cm depth of wood chips for absorbent bedding, and covered with a ventilated filtered plastic cage top. Cages were placed in a rectangular frame containing a grid of 12 photocell beams in an 8×4 configuration (Kinder Scientific, Poway, Calif.) that is positioned 2.5 centimeters from the floor of the cage for the detection of body movements (ambulations) and recorded by computer.

Male human D1 receptor knock-in mice are placed in chambers and allowed to habituate to the chambers for 60 min. During the habituation period, the mice show decreasing locomotion over time, as expected. Following administration of a compound of the invention, animal movement is found to increase in a dose-dependent fashion.

The mice are randomly assigned to treatment groups. In the dose response study, each mouse is placed individually into one of the locomotor activity boxes for a 60 min. habituation period. The mice are then dosed orally using test compound in a 20% hydroxypropyl-betacyclodextrin vehicle and using a 10 mL/kg dose volume. After dosing, the mice are placed back into the LMA boxes and the total number of ambulations is recorded per 10 min interval for each mouse over a 60 min measurement period. Statistical analysis is carried out using one-way ANOVA followed by post-hoc analysis using Dunnett's Comparison test.

The compounds of Example 1 and 8 are assayed essentially as described above and are found to increase basal movement in a dose dependent manner (Tables 7 and 8).

TABLE 7

| Example 1 (dose, mg/kg, PO) | Basal Locomotor Activity (Total Ambulations for 60 min) Means (SEM, % SE), N = 8/group |
|---|---|
| 0.0 (Vehicle - 20% hydroxypropyl-beta-cyclodextrin) | 541 (98, 18%) |
| 1.0 | 410 (113, 28%) |
| 3.0 | 490 (67, 14%) |
| 6.0 | 1517* (324, 21%) |
| 10 | 2426*** (596, 25%) |
| 30 | 3568**** (387, 11%) |

Statistical analysis is done on Total Ambulation data after Log10 Transformation.
One-way ANOVA:
*p < 0.05,
***p < 0.001,
****p < 0.0001,
(Dunnett's Multiple Comparison Test: compared to Vehicle Control on log10 transformed data)

TABLE 8

| Example 8 (dose, mg/kg, PO) | Basal Locomotor Activity (Total Ambulations for 60 min) Means (SEM, % SE), N = 8/group |
|---|---|
| 0.0 (Vehicle - 20% hydroxypropyl-beta-cyclodextrin) | 614 (105, 17%) |
| 3.0 | 335 (59, 18%) |
| 10 | 753 (159, 21%) |
| 20 | 3629* (690, 19%) |
| 30 | 3746** (463, 12%) |
| 60 | 4080 *** (664, 16%) |

Statistical analysis is done on Total Ambulation data after Log10 Transformation.
One-way ANOVA:
*p < 0.05,
**p < 0.01,
*** p < 0.001,
(Dunnett's Multiple Comparison Test: compared to Vehicle Control on log10 transformed data)

The Basal Locomotor Activity data for Example 1 and 8 shown in Table 7 and 8 illustrate that compounds of the invention, and Example 1 and 8 in particular, are effective in locomotor activation of animals that are habituated to the environment. This activity is believed to be the result of central activation of D1 receptors via allosteric potentiation (See e.g. Svensson et al., J. Pharmacol. Exp. Ther. (2017) 360:117-128). The data provided in Tables 7 and 8 for Examples 1 and 8 illustrate the pharmacologically advantageous in vivo efficacy of the compounds of the invention for the potentiation of endogenous dopamine mediated responses. The data provided in Table 7 and 8 for Examples 1 and 8, further illustrate the pharmacologically advantageous oral bioavailability of Examples 1 and 8 and the compounds of formula I.

Plasma and Brain Levels

Example 1 is orally dosed to male mouse from 1 mg/kg to 30 mg/kg in fed condition, and the plasma and brain concentration are determined 1.5 hr post-dose. The fraction unbound of the compound is determined in vitro as described previously (Zamek-Gliszczynski M J, Ruterbories K J, Ajamie R T, Wickremsinhe E R, Pothuri L, Rao M V, Basavanakatti V N, Pinjari J, Ramanathan V K, Chaudhary A K (2011) Validation of 96-well equilibrium dialysis with non-radiolabeled drug for definitive measurement of protein binding and application to clinical development of highly-bound drugs. J Pharm Sci 100: 2498-2507). The ratio (Kpuu) of unbound brain concentration (Cu,brain) vs. unbound plasma concertation (Cu,plasma) is determined as described previously (Raub T J, Wishart G N, Kulanthaivel P, Staton B A, Ajamie R T, Sawada G A, Gelbert L M, Shannon H E, Sanchez-Martinez C, De Dios A (2015) Brain Exposure of Two Selective Dual CDK4 and CDK6 Inhibitors and the Antitumor Activity of CDK4 and CDK6 Inhibition in Combination with Temozolomide in an Intracranial Glioblastoma Xenograft. Drug Metab Dispos. 43:1360-71). The data presented below for Example 1 are averages from 3 animals at each dose. "Con." refers to concentration.

| Dose mg/kg | Time hr | Plasma con. nM | Brain con. nM | fu, plasma | fu, brain | Cu, plasma nM | Cu, brain nM | Kpuu |
|---|---|---|---|---|---|---|---|---|
| 1 | 1.5 | 6.74 | BQL | 0.027 | 0.025 | 0.182 | BQL | NA |
| 3 | 1.5 | 86.6 | 60 | 0.027 | 0.025 | 2.34 | 1.5 | 1.06 |
| 6 | 1.5 | 173 | 129 | 0.027 | 0.025 | 4.67 | 3.22 | 0.65 |
| 10 | 1.5 | 120 | 57.6 | 0.027 | 0.025 | 3.23 | 1.44 | 0.44 |
| 30 | 1.5 | 1660 | 794 | 0.027 | 0.025 | 44.9 | 19.9 | 0.65 |

BQL, below the quantitative limit 1 ng/mg tissue.

Example 8 was orally dosed to male mouse from 3 mg/kg to 60 mg/kg in fed condition, and the plasma and brain concentration was determined 1 hr post-dose. The fraction unbound of the compound was determined in vitro as described previously (Zamek-Gliszczynski M J, et al., Validation of 96-well equilibrium dialysis with non-radiolabeled drug for definitive measurement of protein binding and application to clinical development of highly-bound drugs, J. Pharm. Sci. (2011) 100: 2498-2507). The ratio (Kpuu) of unbound brain concentration (Cu,brain) vs. unbound plasma concertation (Cu,plasma) was determined as described previously (Raub T J, et al., Brain Exposure of Two Selective Dual CDK4 and CDK6 Inhibitors and the Antitumor Activity of CDK4 and CDK6 Inhibition in Combination with Temozolomide in an Intracranial Glioblastoma Xenograft. Drug Metab. Dispos. (2015) 43:1360-71). The data presented below for Example 8 are averages from 3 animals at each dose.

| Dose mg/kg | Time hr | Plasma con. nM | Brain con. nM | fu, plasma | fu, brain | Cu, plasma nM | Cu, brain nM | Kpuu |
|---|---|---|---|---|---|---|---|---|
| 3 | 1.5 | 87.4 | 66.3 | 0.031 | 0.01 | 2.71 | 0.66 | 0.24 |
| 10 | 1.5 | 901 | 267 | 0.031 | 0.01 | 27.9 | 2.67 | 0.10 |
| 20 | 1.5 | 2442 | 721 | 0.031 | 0.01 | 75.7 | 7.21 | 0.10 |
| 30 | 1.5 | 10321 | 2391 | 0.031 | 0.01 | 320 | 23.9 | 0.07 |
| 60 | 1.5 | 20077 | 5000 | 0.031 | 0.01 | 622 | 50 | 0.08 |

Compounds of the invention, for instance Example 1, show an advantageous combination of pharmacological properties, such as potentiation of human D1 receptor signaling in response to dopamine, high oral in vivo availabilty, in vivo efficacy in locomotor activation of animals that are habituated to the environment, and a favorable toxicity profile in preclinical testing. For instance Example 1 demonstrates potentiation of human D1 receptor signaling in response to dopamine (16.4±3.18 nM (n=10)), and significant in vivo efficacy when orally administered at 6, 10, and 30 mg/kg PO, in locomotor activation of human D1 receptor knock-in mice that are habituated to the environment, also illustrating the favorable oral bioavailability of this compound. Further, Example 1 is generally well tolerated when administered in vivo to normal rats over a broad dose range, and shows an advantageous lack of toxicity in this in vivo experiment. Thus, Example 1 demonstrates an advantageous combination of favorable pharmacological properties supporting possible use as an orally administered therapeutic agent for dopamine D1 receptor potentiaion, and treatment for Parkinson's disease, Schizophrenia, ADHD, and/or Alzheimer's disease.

We claim:
1. A compound of the formula:

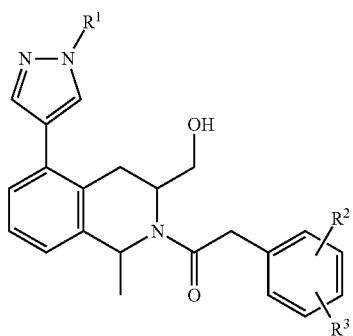

wherein:
$R^1$ is —H, —$CH_3$, —$CH_2CH_3$, —$CH_2CH_2OH$,

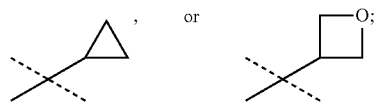

$R^2$ is —F or —Cl; and
$R^3$ is —H, —F or —Cl;
or a pharmaceutically acceptable salt thereof.

2. The compound according to claim 1 of the formula:

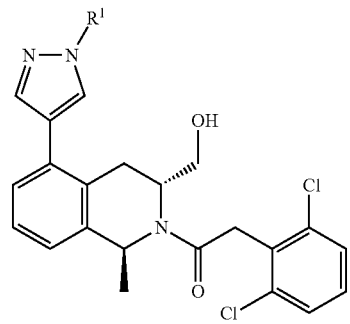

wherein:

R¹ is —H, —CH₃, —CH₂CH₃, —CH₂CH₂OH,

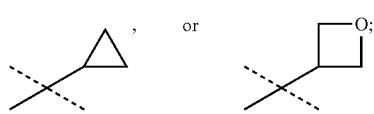

or a pharmaceutically acceptable salt thereof.

3. The compound of claim 1 selected from the group consisting of:

2-(2,6-dichlorophenyl)-1-((1S,3R)-5-(1-ethyl-1H-pyrazol-4-yl)-3-(hydroxymethyl)-1-methyl-3,4-dihydroisoquinolin-2(1H)-yl)ethan-1-one;

1-((1S,3R)-5-(1-cyclopropyl-1H-pyrazol-4-yl)-3-(hydroxymethyl)-1-methyl-3,4-dihydroisoquinolin-2(1H)-yl)-2-(2,6-dichlorophenyl)ethan-1-one;

2-(2,6-dichlorophenyl)-1-((1S,3R)-3-(hydroxymethyl)-1-methyl-5-(1-(oxetan-3-yl)-1H-pyrazol-4-yl)-3,4-dihydroisoquinolin-2(1H)-yl)ethan-1-one;

1-((1S,3R)-5-(1-(2-(l1-oxidaneyl)ethyl)-1H-pyrazol-4-yl)-3-(hydroxymethyl)-1-methyl-3,4-dihydroisoquinolin-2(1H)-yl)-2-(2-chlorophenyl)ethan-1-one;

2-(2-chloro-6-fluorophenyl)-1-((1S,3R)-3-(hydroxymethyl)-1-methyl-5-(1-(oxetan-3-yl)-1H-pyrazol-4-yl)-3,4-dihydroisoquinolin-2(1H)-yl)ethan-1-one;

2-(2-chlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one;

2-(2,6-dichlorophenyl)-1-((1S,3R)-3-(hydroxymethyl)-1-methyl-5-(1H-pyrazol-4-yl)-3,4-dihydroisoquinolin-2(1H)-yl)ethan-1-one;

2-(2-chloro-6-fluorophenyl)-1-((1S,3R)-3-(hydroxymethyl)-1-methyl-5-(1H-pyrazol-4-yl)-3,4-dihydroisoquinolin-2(1H)-yl)ethan-1-one;

2-(2,6-difluorophenyl)-1-((1S,3R)-3-(hydroxymethyl)-1-methyl-5-(1H-pyrazol-4-yl)-3,4-dihydroisoquinolin-2(1H)-yl)ethan-1-one;

2-(2-chloro-5-fluorophenyl)-1-((1S,3R)-3-(hydroxymethyl)-1-methyl-5-(1H-pyrazol-4-yl)-3,4-dihydroisoquinolin-2(1H)-yl)ethan-1-one;

2-(2-chloro-4-fluorophenyl)-1-((1S,3R)-3-(hydroxymethyl)-1-methyl-5-(1H-pyrazol-4-yl)-3,4-dihydroisoquinolin-2(1H)-yl)ethan-1-one;

2-(2-fluorophenyl)-1-((1S,3R)-3-(hydroxymethyl)-1-methyl-5-(1H-pyrazol-4-yl)-3,4-dihydroisoquinolin-2(1H)-yl)ethan-1-one;

2-(2,3-difluorophenyl)-1-((1S,3R)-3-(hydroxymethyl)-1-methyl-5-(1H-pyrazol-4-yl)-3,4-dihydroisoquinolin-2(1H)-yl)ethan-1-one; and 2-(2,5-difluorophenyl)-1-((1S,3R)-3-(hydroxymethyl)-1-methyl-5-(1H-pyrazol-4-yl)-3,4-dihydroisoquinolin-2(1H)-yl)ethan-1-one;

or a pharmaceutically acceptable salt thereof.

4. The compound which is:

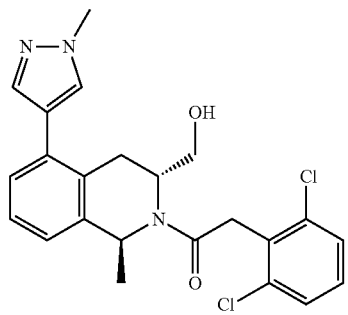

or a pharmaceutically acceptable salt thereof.

5. The compound of claim 4 which is:

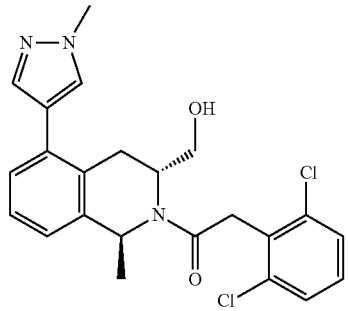

6. A compound which is 2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one hydrobromide monohydrate.

7. A compound of claim 6 which is crystalline 2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one hydrobromide monohydrate.

8. A compound of claim 7 which is crystalline 2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one hydrobromide monohydrate characterized by an X-ray powder diffraction pattern using CuKα radiation having a diffraction peak at diffraction angle 2-theta of 17.4 in combination with one or more of the peaks selected from the group consisting of 27.0, 18.3, and 21.7; with a tolerance for the diffraction angles of 0.2 degrees.

9. A pharmaceutical composition comprising a compound according to any one of claims 1 to 3, or a pharmaceutically acceptable salt thereof, and a pharmaceutically acceptable carrier, diluent or excipient.

10. A pharmaceutical composition comprising:

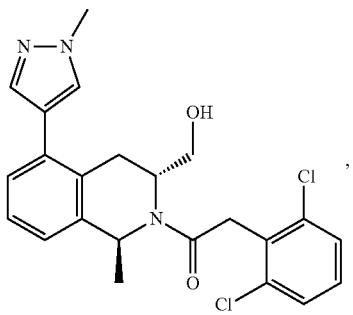 [SMILES: C[C@H]1c2cccc(-c3cnn(C)c3)c2C[C@H](CO)N1C(=O)Cc1c(Cl)cccc1Cl]

or a pharmaceutically acceptable salt thereof, and a pharmaceutically acceptable carrier, diluent or excipient.

11. A pharmaceutical composition of claim 10 comprising:

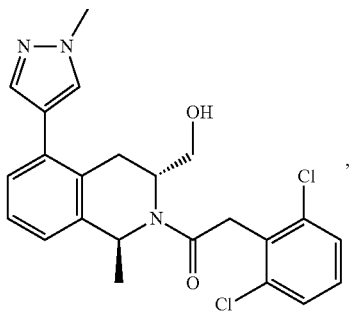 [SMILES: C[C@H]1c2cccc(-c3cnn(C)c3)c2C[C@H](CO)N1C(=O)Cc1c(Cl)cccc1Cl]

and a pharmaceutically acceptable carrier, diluent or excipient.

12. A pharmaceutical composition comprising 2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one hydrobromide monohydrate, and a pharmaceutically acceptable carrier, diluent or excipient.

13. A method of treating Parkinson's disease comprising administering to a patient in need thereof an effective amount of a compound according to any one of claims 1-3, or a pharmaceutically acceptable salt thereof.

14. A method of treating Parkinson's disease comprising administering to a patient in need thereof an effective amount of a compound which is 2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one, or a pharmaceutically acceptable salt thereof.

15. A method of treating Alzheimer's disease comprising administering to a patient in need thereof an effective amount of a compound according to any one of claims 1-3, or a pharmaceutically acceptable salt thereof.

16. A method of treating Alzheimer's disease comprising administering to a patient in need thereof an effective amount of a compound which is 2-(2,6-dichlorophenyl)-1-((1S,3R)-3-(hydroxymethyl)-1-methyl-5-(1-methyl-1H-pyrazol-4-yl)-3,4-dihydroisoquinolin-2(1H)-yl)ethan-1-one, or a pharmaceutically acceptable salt thereof.

\* \* \* \* \*